US007350535B2

(12) United States Patent
Liepold et al.

(10) Patent No.: US 7,350,535 B2
(45) Date of Patent: Apr. 1, 2008

(54) VALVE

(75) Inventors: Gerhard Liepold, Watchung, NJ (US); Dietrich Bizer, Madison, NJ (US)

(73) Assignee: GL Tool and Manufacturing Co. Inc., Livingston, NJ (US)

( * ) Notice: Subject to any disclaimer, the term of this patent is extended or adjusted under 35 U.S.C. 154(b) by 407 days.

(21) Appl. No.: 10/512,510

(22) PCT Filed: Apr. 25, 2003

(86) PCT No.: PCT/US03/12924

§ 371 (c)(1),
(2), (4) Date: Oct. 26, 2004

(87) PCT Pub. No.: WO03/090842

PCT Pub. Date: Nov. 6, 2003

(65) Prior Publication Data

US 2005/0150546 A1    Jul. 14, 2005

Related U.S. Application Data

(60) Provisional application No. 60/375,747, filed on Apr. 26, 2002.

(51) Int. Cl.
*F16K 17/40*   (2006.01)
(52) U.S. Cl. .................... 137/68.19; 137/553; 251/93; 251/106
(58) Field of Classification Search ............ 137/68.19, 137/68.21, 68.29, 68.3, 553, 556.6; 251/92, 251/93, 108, 252, 266, 274
See application file for complete search history.

(56) References Cited

U.S. PATENT DOCUMENTS

| | | | | |
|---|---|---|---|---|
| 214,367 A | * | 4/1879 | Colvin | 251/108 |
| 988,378 A | * | 4/1911 | Olson | 251/91 |
| 2,426,808 A | * | 9/1947 | Auer | 137/68.19 |
| 2,642,256 A | * | 6/1953 | Stehlin | 251/252 |
| 2,712,881 A | * | 7/1955 | Mathisen | 137/68.19 |
| 3,038,485 A | * | 6/1962 | Hosek | 137/68.19 |
| 3,039,482 A | * | 6/1962 | Goldberg | 137/68.27 |
| 3,219,047 A | * | 11/1965 | Kircher, III et al. | 137/68.19 |
| 3,223,100 A | * | 12/1965 | Koenig et al. | 137/68.3 |
| 3,424,181 A | * | 1/1969 | Morse | 137/68.3 |
| 3,525,350 A | * | 8/1970 | Hosek | 137/68.19 |
| 4,064,003 A | * | 12/1977 | Newton | 137/68.3 |
| 4,294,247 A | * | 10/1981 | Carter et al. | 137/68.19 |
| 6,170,800 B1 | | 1/2001 | Meloul et al. | |
| 6,354,466 B1 | | 3/2002 | Karpisek | |

* cited by examiner

FOREIGN PATENT DOCUMENTS

GB    1 573 482    8/1980

*Primary Examiner*—John Rivell
(74) *Attorney, Agent, or Firm*—Hoffman & Baron, LLP

(57) ABSTRACT

A valve apparatus (100) for use in sterile fluid transfer or isolator systems has open entry (10) and exit (11) sides and a passageway (9) for fluid between the entry (10) and the exit (11) sides. The entry side (10) is connectable to an opening (4c) of a vessel or pipe (4) and the exit side (11) is connectable to downstream processing by means such as tubing, a vessel or a pipe. The entry side (10) includes a rupturable seal (2a) blocking the open entry side (10). Valve (100) also includes an actuator (5) attached to a piston (1) which moves within the valve (100), the piston being connected to the seal so that on movement of the piston, the seal is torn free from the entry side thereby allowing fluid gain entry to the valve (100) and to pass along the passageway (9) between the open entry (10) and exit (11) sides to downstream processing.

31 Claims, 20 Drawing Sheets

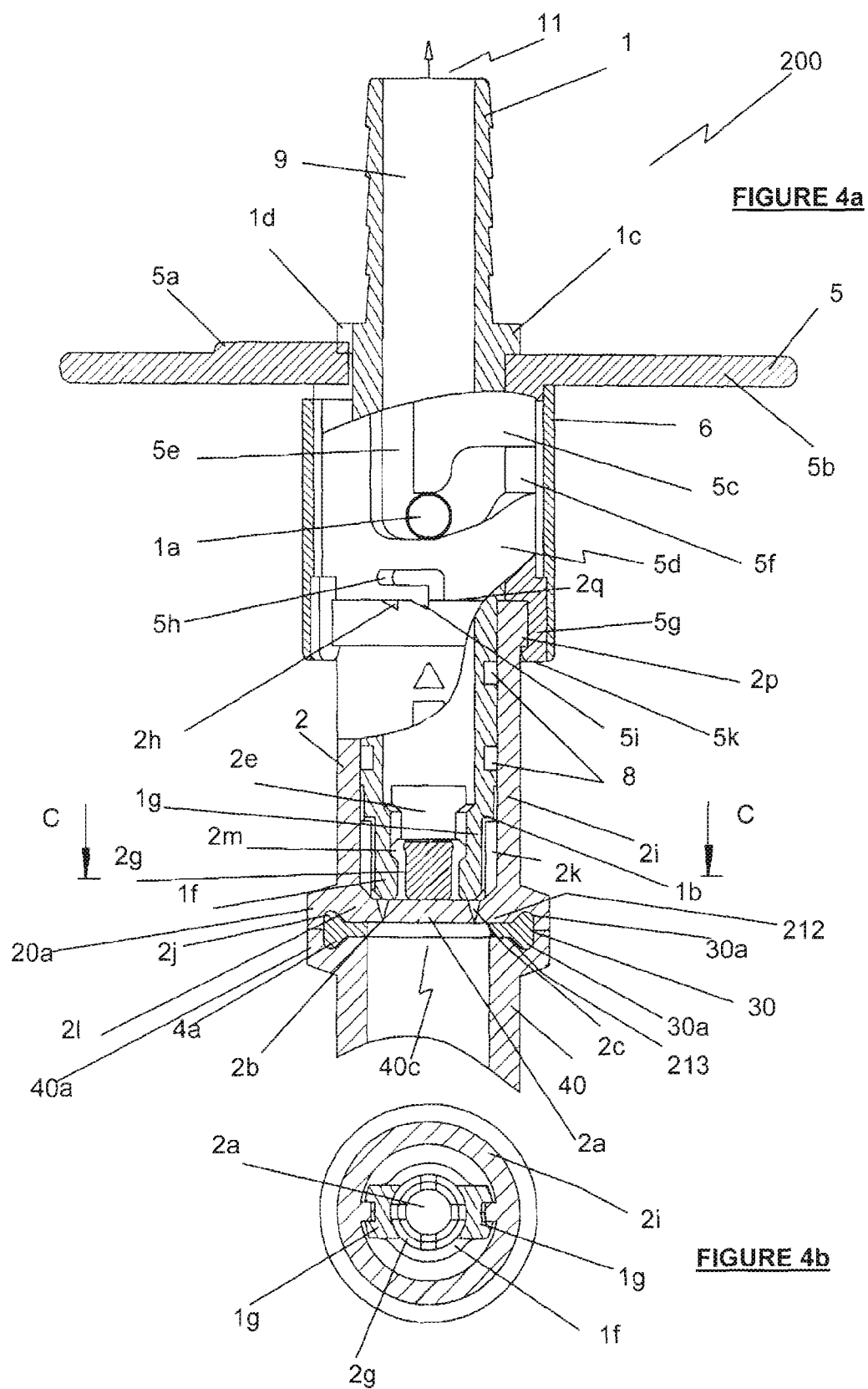

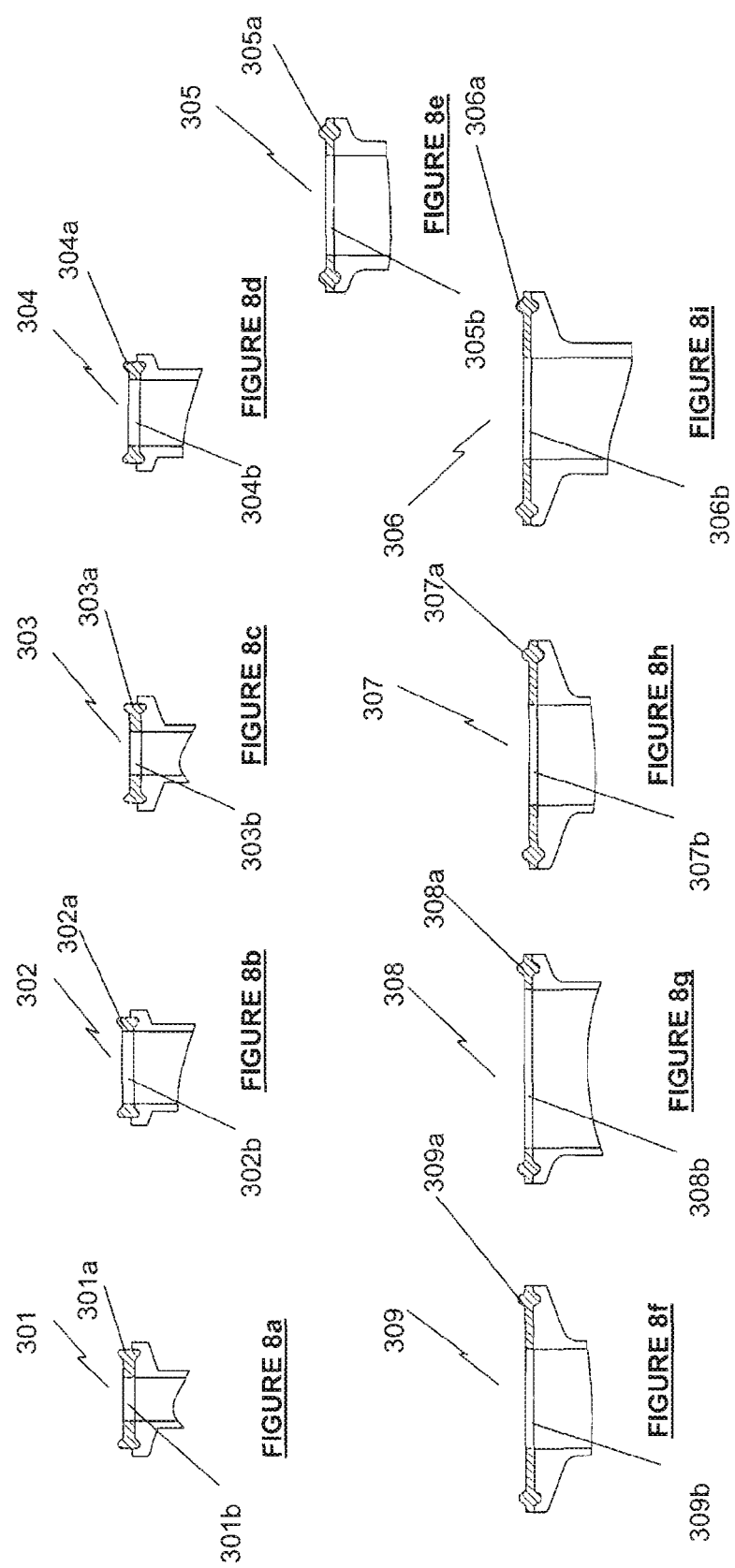

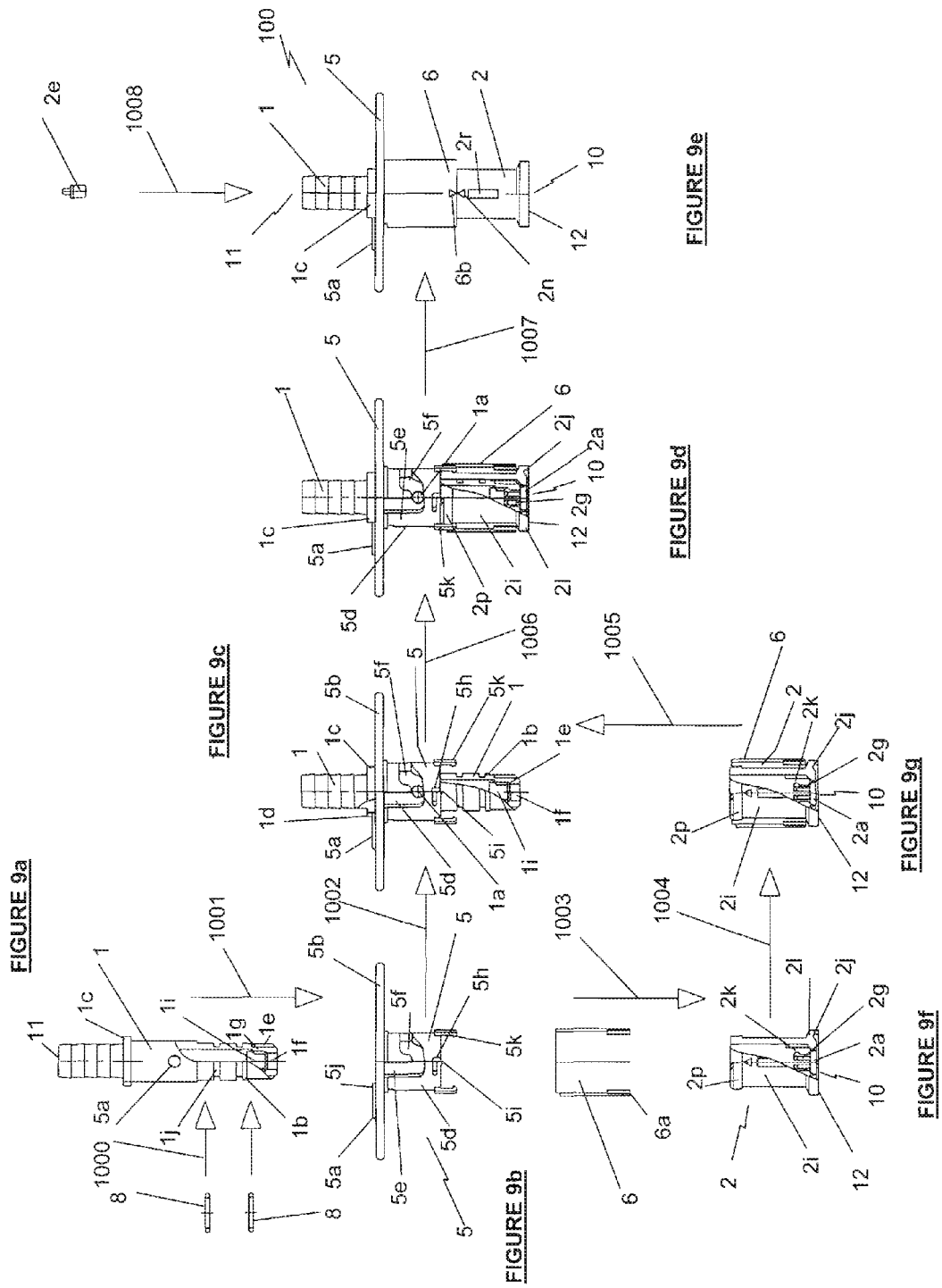

VALVE

CROSS-REFERENCE TO RELATED APPLICATIONS

This application is the national stage filing under 35 U.S.C. §371 of PCT/US02/12924, filed Apr. 25, 2003, which claims priority to U.S. No. 60/375,747, filed Apr. 26, 2002 which is incorporated herein by reference.

FIELD OF THE INVENTION

The present invention relates to a valve apparatus and in particular to a valve apparatus useful in systems for the sterile transfer of fluids.

BACKGROUND OF THE INVENTION

Validation and accountability are vital in most scientific industries and especially so in the pharmaceutical and biotechnological industries. A major challenge to these industries is the need to demonstrate accurately and reproducibly that sterility is achieved and maintained throughout production lines within a plant. This must be done in a manner which meets the stringent requirements of regulatory bodies such as the United States FDA. Acceptable standards can be difficult to be met when a substance is transferred from one sterile location to another sterile location by non direct means.

One current practice includes provides a holding vessel into which substance can be transferred by means of a connecting valve. The holding vessel is transferred to the second sterile location and the substance is then transferred from the holding vessel into the second sterile location via one or more connecting valves. The connecting valves and holding vessel can be sterilised using conventional techniques such as gas, radiation or steam sterilisation. However during connection of the connecting valve to the first sterile location, the external connecting surface of the connecting valve is exposed to the atmosphere and sterility of the valve is compromised.

Alternative methods of substance transfer suffer from similar problems.

For example, in the use of an autoclavable port, where a non-sterile male port is attached to an empty non-sterile bulk vessel prior to sterilization, the entire assembled apparatus is then sterilised by autoclaving. However, a major disadvantage of this technique is that the vessel must be empty before sterilisation.

Alternatively, an irradiated port can be used, where a non-sterile male port is attached to an empty non-sterile disposable bag prior to sterilisation of the whole by irradiation. Again a major disadvantage associated with this system is that the bag must be empty before sterilisation.

A further method of substance transfer involves connecting a transfer port to a vessel under aseptic conditions. With this method it is irrelevant whether or not the vessel is empty or filled. However despite the necessity to undertake these actions in a designated 'Grade A' zone, there is an increased risk of contamination due to the making and breaking of various connections. The mere fact that a 'Grade A' zone is required to complete these actions requires a significant financial investment by a company wishing to employ this technique.

Another technique incorporates the use of a tube fuser. A sterile bulk vessel is attached to tubing emanating from a sterile port through a tube fuser. This technique is undesirable for numerous reasons including the restricted choice of tubing. This in turn limits the types of substance that can be transferred through the tubing. It is also undesirable to use wetted tubing. Furthermore there is also a potential risk of cross-contamination and re-contamination.

Despite the numerous attempts to find a sterile method of substance transfer none have been wholly successful. In all of the above techniques the sterility of the port or valve used to transfer the substance from one vessel to another is compromised during the connection process or is susceptible to contamination. This is undesirable and leads to problems when validating a product.

Piston-operated valves for the above applications are known. These act by moving a piston up and down or sliding over and back within an apertured housing so as to cover or uncover the fluid communication apertures of the housing. O-ring seals are provided for sealing between the open and closed valve positions. Such valves therefore have slots for receiving the O-rings and the difficulties of assuring that these slots and the spaces about them are not subject to contamination render them questionable for use in sterile transfer systems.

OBJECTS OF THE INVENTION

It is an object of the present invention to seek to alleviate the aforementioned problems.

SUMMARY OF THE INVENTION

Accordingly, the present invention provides a valve comprising a body having first and second open ends and a passageway for fluid between the ends, the first end including a coupling means for sealingly connecting the body about an opening of an external device and a seal blocking the open area of the first end which in use is placeable in register with the opening of the external device, the valve further including a seal displacement means movable within the body so as to interrupt the seal permitting fluid to pass along the passageway between the ends, the coupling means and seal presenting an external sterilisable mating surface for sealingly mating with a mating surface about the opening in the external device. Ideally, the displacement means comprises a means for rupturing the seal so as to allow fluid communication between the interiors of the body and the external device.

In a preferred arrangement the seal is formed integrally with the coupling means at the sterilisable external surface. Ideally, a junction is provided between the coupling means and the seal and comprises at least one weakened fracture line so that when the rupturing means moves within the body it breaks the seal along at least a portion of the at least one fracture line. Preferably, the junction or fracture line comprises an area of reduced thickness of the mating surface. Ideally, the fracture line is endless and encloses the seal, which may be punched or stamped out of the coupling means or torn free therefrom. In a particularly preferred arrangement the fracture line is in the shape of a circle and the seal is disc shaped, and when the rupturing means is moved, it causes the disc shaped seal to be displaced from its position blocking the opening of the first end.

The rupturing means may be arranged to break the seal either by puncturing through it or stamping through it outwardly, or by gripping it and withdrawing the seal or a portion of it away from the mating surface. For this purpose, mutually engageable gripping means are ideally provided on the seal and rupturing means. In a preferred arrangement, the rupturing means is moveable within the body of the valve in a direction from the first end toward the second end so that on movement of the rupturing means, the gripped seal is broken free from the coupling means and withdrawn into the interior of the body.

Ideally, the gripping means include at least one finger element projecting into the valve interior from the inner surface of the seal and a receiver element provided on the rupturing means for securely receiving and retaining the finger element. One suitable arrangement provides a plurality of fingers which are shaped to snap-fit onto a retaining portion of the rupturing means.

The rupturing means may conveniently comprise a piston. Most conveniently the piston is hollow and has an open end comprising the second open end of the valve body.

Ideally, the coupling means includes an upstanding cylindrical portion within which the piston moves. Conveniently, the piston is disposed within the cylindrical portion and one or more sealing means are positioned between the external surface of the piston and the internal surface of the cylindrical portion. This provides an effective seal between the piston and the cylindrical portion, preventing fluid from passing into or out of the area intermediate the piston and the cylindrical portion. Ideally, the piston sealing means comprises O-ring or mating sealing edges. Any other sealing mechanism know to a person skilled in the art can also be used.

One or more apertures are provided in the wall of the piston adjacent the seal so that fluid may pass between the interior of the piston and the first end via the or each aperture.

In an advantageous arrangement, the base of the piston, close to the seal, includes a depending ring portion and the fingers projecting upwardly from the seal have projections at their tips which snap onto the ring to retain the seal and piston securely connected together. These fingers are preferably resiliently biased into the engaged position. As a further security measure, a plug may be provided to be receivable between the fingers so as to lock them into their position engaged with the piston. The ring portion ideally has a reduced external diameter compared to the external diameter of the base of the piston so that the passage of fluid to the interior of the piston after removal of the seal is facilitated.

Advantageously, an actuation means is provided for moving the piston between a ready state in which the seal is intact and the valve is closed and a deployed state in which the seal is broken and moved with the piston away from the mating surface into the cylindrical portion of the coupling means so that the valve is open.

Advantageously, the second end of the body is attachable to a pipe, pipeloop, multiple pipe connections or vessel to or from which fluid is transferred.

Advantageously, the seal may be provided either as a surface continuous with the coupling means at the entry side (first end) of the valve body or as an attachment which is attachable to the entry side. If the seal is being provided as an attachment, it ideally has a shape that fits the entry side of the housing thereby providing a secure connection that prevents fluid from flowing into the valve. In one convenient arrangement the attachment is in the shape of a disc. It may be formed and shaped to provide a secondary function of acting as a sealing washer between the valve and vessel to which it is coupled when the valve and vessel are secured together. Advantageously the seal is formed from an appropriate plastics material such as polypropylene and may be coated with a non-stick material such as TEFLON™. The material of the seal is not limited to plastics materials and any suitable material known to a person skilled in the art can be used. Ideally the material selected will have received approval for use in the pharmaceutical or biotechnological industries from an appropriate regulatory authority. Plastics, rubber, metal, foil and other seals, whether flexible and/or stretchable or not, are all contemplated to be useful within the scope of the invention.

Advantageously, the actuation means include a handle operable by a user and a collar portion connected to the cylindrical portion of the coupling means and to the piston for effecting relative movement between the cylindrical portion and the piston. Ideally, the piston and gripped seal are withdrawn into the cylindrical portion of the coupling means as the actuator moves the piston from the ready (valve closed) state to the deployed (valve open) state. It is preferable for the actuation means to include a safety lock means for preventing undesired such relative movement. Ideally the safety lock means comprises a tongue releasably engageable with the piston for preventing movement from the ready state to the deployed state. The safety lock means prevents movement of the actuation means, however once released, the actuation means are free to activate the piston and rupture the seal. The actuation means and safety locking device are not limited to those described above and alternative suitable actuation means and/or safety lock means may be selected.

When the handle is turned, the piston is driven by the actuator collar to move in a direction away from the seal location at the first end (or entry side) of the housing causing the seal to rupture and fluid to gain entry to the valve interior. As the piston moves in this direction, it pulls the attached seal with it so that the seal breaks along the fracture line and the seal is carried into the cylindrical portion. Fluid can then flow, via the apertures in the piston wall between the first and second (or entry and exit) ends of the valve.

Stop means are provided for preventing the actuator from moving in a reverse direction which would return the value from the deployed (open) state to the ready (closed) state. This has the advantage that the valve may not inadvertently or mischievously be returned to a closed state having previously been open and accordingly, a user knows that when the valve is closed, it cannot have previously been compromised by an unknown opening.

Usefully, visible or tactile indication means are provided on the valve for indicating to a user the position of the valve between the ready and deployed states. Furthermore, means are provided for moving the valve into an intermediate position between the ready and deployed states. In the intermediate position, the valve remains closed with the seal intact, but the lock which retains the valve closed has been released. Means are provided for retaining the valve in this intermediate condition and the indication means are useful for alerting the user to the fact that this intermediate condition is assumed.

Advantageously, the valve can be provided as a single-use disposable valve or as a multi-use valve.

Conveniently, a single-use disposable valve is fabricated from an appropriate plastics material, optionally coated with a non-stick coating such as TEFLON™.

Advantageously a muiti-use valve has component, parts which are fabricated from an appropriate heavy duty material such as stainless steel or the like. Ideally, in this case the seal is provided as a replaceable component and is formed from an appropriate plastics material optionally coated with silicon or other non-stick material such as TEFLON™ or as a metal, foil, rubber or other membrane. The seal can be used one or more times depending on its nature and provided that the integrity of the seal per se is not compromised on opening the valve. After each use the seal is removed and cleaned or replaced, the valve is cleaned and the new or cleaned unbroken seal is inserted into the appropriate position. If the same seal is used several times, it is preferable that it be discarded after about five uses and replaced with a new seal, in order to maintain the integrity of the system. Obviously, if the seal is of the type which is punctured when the piston drives through it, then it will have to be replaced for each use.

The materials of the valve are selected so that the valve can be sterilised using suitable techniques known in the art, such as gamma ray, ethylene oxide gas or steam sterilisation, prior to use.

The valve is supplied sterile and packed. This package may include other components to be used in a sterile transfer process. In order to use it, the package is opened and the valve is removed, causing the mating surface at the first (entry side) end to become contaminated. This external surface is connected by the coupling means to an external line or vessel so that the valve first end opening and the opening to the interior of the line or vessel are in register, with the seal closing the space between them. The contaminated external surfaces of the seal is then steam sterilised together with the interior of the line or vessel. Thereafter, the valve may be opened.

Once the contaminated external face of the seal has been resterilised, the lock means of the actuator is released and the actuation means is operated to cause the piston to break the seal enabling fluid flow between the vessel and the valve. Obviously, the other, second, open end of the valve will also be connected to a vessel or pipe or the like before opening the valve.

It will be appreciated that the safety lock prevents undesired movement of the actuation means. Accordingly, this lock acts as a warning indicator to a user. If the lock device is engaged while the valve is being attached to the opening of the vessel and/or pipe and remains locked while the sealed entry side of the valve is being resterilised, the user knows definitively that the seal is intact and sterility of the valve is uncompromised. However, if the safety lock is released during the same period, the user knows immediately that the seal may have ruptured and sterility of the valve may be compromised. This enables a user to visually check whether a safe sterile transfer of fluid from one sterile location to another can be attempted.

Suitable materials for fabricating the individual components of the valve include plastics material (for example polypropylene and other suitable sterilisable plastics), metals, ceramics and so on. For a multi-use valve, durable, resterilisable materials such as metals (for example stainless steel) will be particularly suitable.

The invention will now be described more particularly with reference to the accompanying drawings which show, by way of example only, several embodiments of a valve according to the invention.

BRIEF DESCRIPTION OF THE DRAWINGS

In the drawings:

FIG. 1b is a plan view of the first embodiment of the valve of FIG. 1a;

FIG. 1d is a perspective view of the housing of the valve of FIG. 1a;

FIG. 3b is a sectional view along the line B-B of FIG. 3a;

FIG. 4a is a side sectional view of a second embodiment of a single-use valve according to the invention;

FIG. 4b is a side sectional view of the valve along the line C-C of FIG. 4a;

FIGS. 8a to 8i are a series of side sectional views of different sized washers and vessels openings;

FIGS. 9a to 9e show the steps in the assembly of the valve of FIG. 1a;

DETAILED DESCRIPTION OF PREFERRED EMBODIMENTS

Figure 1A:
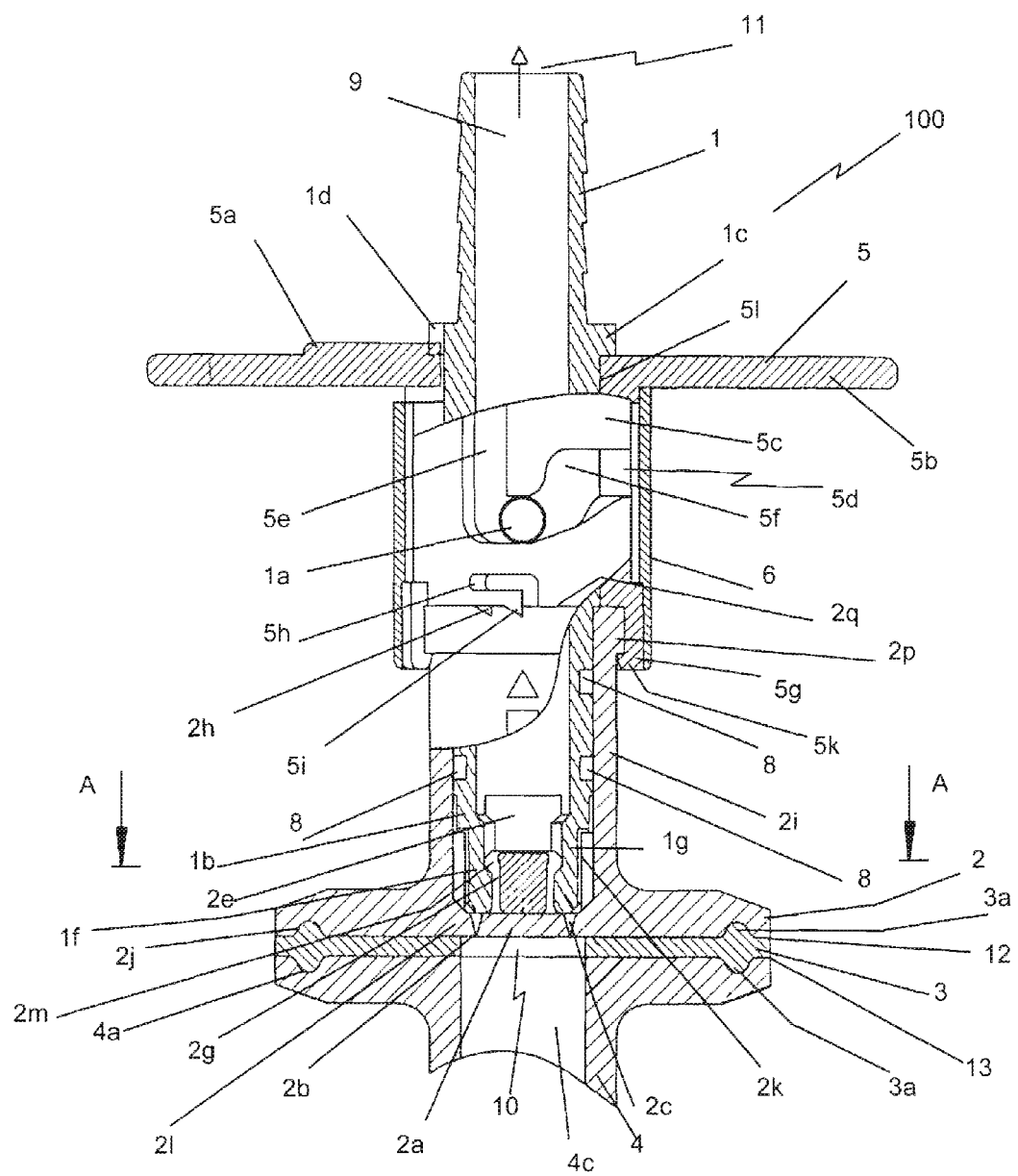
FIG. 1a is a side sectional view of a first embodiment of a single use valve according to the invention.
Figure 1B:
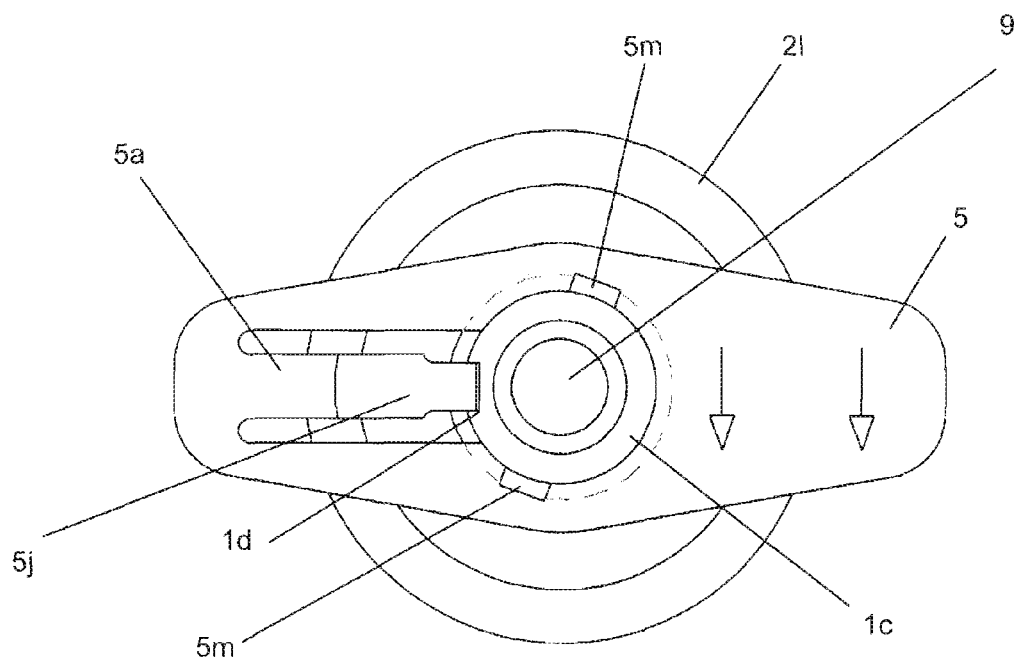
Figure 1C:
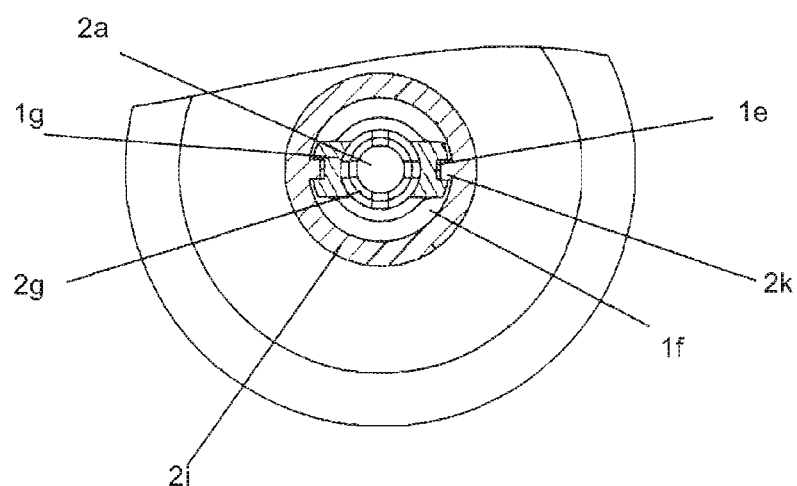
FIG. 1c is a sectional view of the valve along the line. A-A of FIG. 1b.

Referring initially to FIGS. 1a to 1k and FIG. 9, there is shown a first embodiment of a single-use valve 100 according to the invention in its closed state. Valve 100 comprises a housing 2 having a bore for receiving a hollow piston 1.

Valve 100 has an entry side generally designated 10 and an exit side generally designated 11. At the entry side, housing 2 is connectable to a vessel 4 so that the fluid paths of the opening 4c in vessel 4 and fluid path 9 of the valve 100 are in register. Each of the housing 2 and vessel 4 have corresponding mating surfaces 12, 13, which can be connected together in use in the manner described below. For this purpose, housing 2 is conveniently formed with a sleeve region 2i having at one end an outwardly extending flange 21, the base of the flange 21 comprising the mating surface 12. At its other end, sleeve region 2i is provided with a collar 2p, the end face 2q of which includes notches 2f, 2h, 2d. The purposes of the collar 2p and notches 2f, 2h, 2d will be described below. At its exit side 11, the piston 1 extends from the valve 100 and the external surface is couplable to a downstream process, tubing, piping, vessel or the like.

Interconnecting piston 1 and housing 2 is an actuator 5 with locking mechanism 5a. Actuator 5 also comprises a handle 5b by means of which the valve 100 may be moved between open and closed states. Depending from handle 5b is a cam mechanism 5c for enabling the piston to be displaced longitudinally relative to the housing 2 and actuator 5. The entry side of valve 100 is covered with a sterilisable seal 2a. In this embodiment of the invention seal 2a is formed integrally and continually with housing 2.

A cover member 6 is provided about the cam mechanism 5c of the actuator 5. Seal 2a covers the mouth of the valve 100 at the entry side 10 and is formed continuously with the flange 21. Seal 2a is also connected to piston 1 in the matter described below. A junction 2b between the flange 21 and seal 2a is formed on the interior surface of the seal 2a, the interior surface of the seal 2a being that surface facing the piston 1. Junction 2b comprises a weakened point or a fracture line, formed for example by providing a reduction in thickness of the housing 2 in the area 2c. When valve 100 is activated the seal 2a and flange portion 21 separate at junction 2b to provide a fluid passageway through the valve.

The individual components of the valve are shown, disassembled from one another, in FIGS. 1d to 1k.

The valve 100 is opened by releasing locking mechanism 5a and rotating handle 5b in a clockwise direction. Locking mechanism 5a comprises a release clip mechanism formed integrally with handle 5b and includes a tongue 5j. Piston 1 has a radially projecting flange 1c with a recess 1d. When the valve is closed tongue 5j engages in recess 1d thereby preventing rotation of the handle 5b in either a clockwise or anti-clockwise direction. To release the locking mechanism 5a, an external pressure such as a thumb force is applied to tongue 5j to depress it thereby disengaging the tongue 5j from recess 1d. The actuator 5 is then free to rotate.

Rotation of actuator 5 causes piston 1 to move in the direction of the arrow in FIG. 1a, which causes the seal 2a to rupture at the fracture line 2b since the piston 1 and seal 2a are interconnected in the manner described below. This effectively withdraws the piston 1 plus seal 2a into the sleeve region 2i of housing 2 away from the flange 21 thus removing the seal 2a from its position blocking the mouth 10 of the valve and thereby enabling fluid to gain entry into valve 100 as shown in FIG. 3d.

Figure 3A:
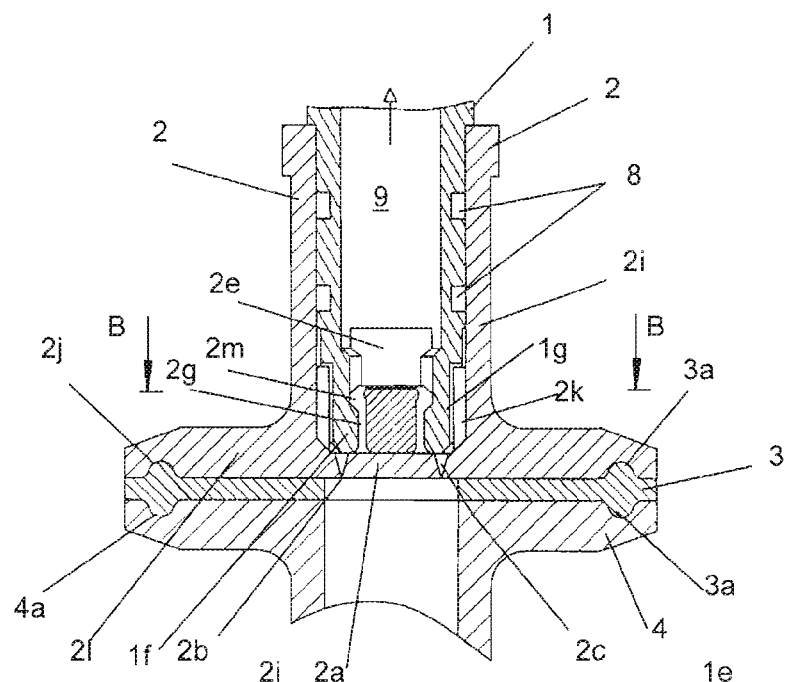
FIG. 3a is a side sectional view of the seal portion of the valve of FIG. 1b prior to activation.
Figure 3B:
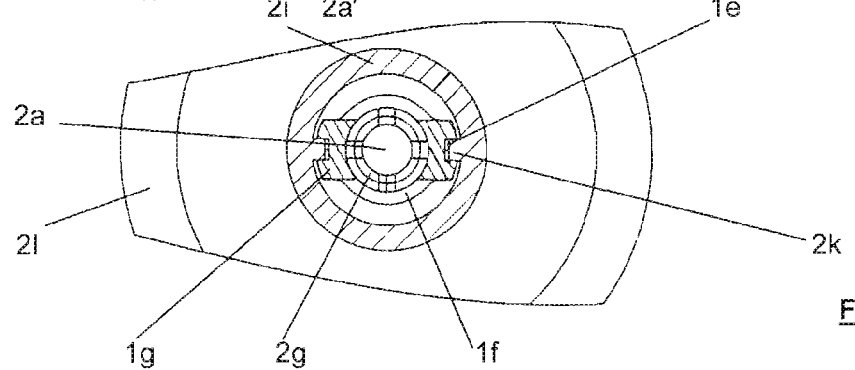
Figure 3C:
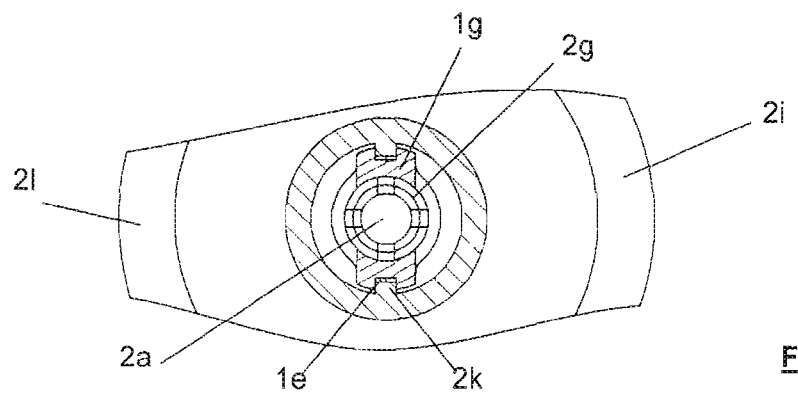
FIG. 3c is a sectional view along the line B-B of FIG. 3a after activation.
Figure 3D:
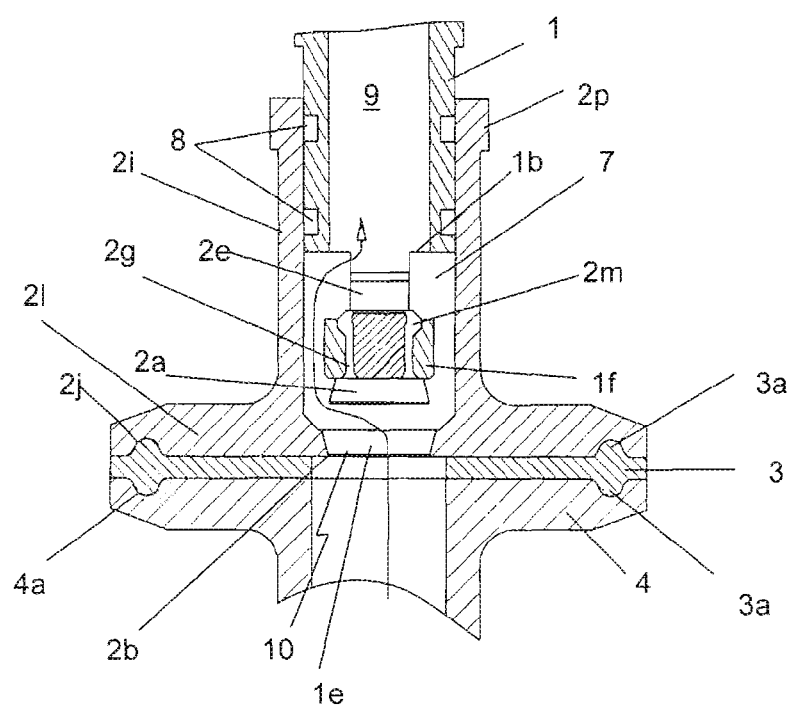
FIG. 3d is a side sectional view of the seal portion of the valve of FIG. 3a after activation.

Thus when valve 100 is opened and as shown more clearly in FIG. 3d, fluid enters chamber 7 through the entry side mouth 10 and passes through collar 2i, into the hollow centre that is the fluid path 9 of piston 1.

A pair of O-rings 8 are positioned on the exterior surface of the piston 1 intermediate piston 1 and the collar region 2i of housing 2. The O-rings 8 seat in grooves 1j (see FIGS. 1h and 1i) and provide an effective seal between piston 1 and housing 2 preventing any fluid passing. The O-rings 8 also provide resistance for the piston 1 as it moves, preventing piston 1 from moving too quickly and overshooting in either direction.

FIG. 1a shows a side section view of valve 100 coupled to an opening 4c of a separate vessel or pipe 4. Both the valve 100 and the opening 4c have matching grooves 2j (see FIGS. 1a and 1e) and 4a respectively that encircle the circumferences of both coupling surfaces 12, 13, the coupling surface 12 of valve 100 being that which includes the sterilisable external surface of the seal 2a. Washer 3 is placed intermediate the coupling surfaces 12, 13 of the valve 100 and opening 4c to seal them together. The washer 3 is formed with a circular formation 3a on both of its planar surfaces. Formation 3a seats in the grooves 2j and 4a respectively to locate the washer 3. The valve 100, washer 3 and vessel 4 can be secured together using a suitable fixing means such as a triclover clamp mechanism (not shown).

The means of interconnecting the piston 1 to the seal 2a will now be described with particular reference to FIGS. 1a, 1c, 1e, 1i, 1j, 3a, 3d and 9. Projecting upwardly from the substantially planar inner face of the seal 2a are a set of four spaced-apart fingers 2g. The free ends of the fingers 2g have a projection 2m facing radially outwards towards the collar region 2i of the housing 2. From the base section 1b of piston 1 depends a circular skirt 1f which is separated from the base section 1b by a pair of opposed spacers 1g thereby providing a pair of fluid flow apertures 1i which constitute a fluid flow passageway to the interior fluid path 9 of the piston 1.

On assembly of the valve 100, the fingers 2g are arranged to project into the skirt 1f until the projections 2m snap over the edge of the skirt adjacent the base 1b and against the inner facing surfaces of the spacers 1g. The fingers 2g are resiliently outwardly biased so as to retain the projections 2m in engagement with the piston 1. As an extra measure to retain the connection between the seal 2a and the piston 1, a plug 2e is provided to be received between the bases of the finger 2m and to further bias them into the radially outward position in which the seal 2a is locked together with the piston 1. Thus, the seal 2a is permitted to move only on displacement of the piston 1 to which it is connected.

The matching interior surfaces of collar portion 2i of the housing 2 and exterior surfaces of the spacers 1g have complementary ribs 2k and recesses 1e respectively to correctly guide and locate the piston 1 over the fingers 2g.

It will be appreciated from the foregoing that on displacement of the piston 1 in the direction of the arrow in FIG. 1a, the seal 2a which is locked to the piston 1 will be torn along the weakened junction 2b until it separates from the flange 21 and will be withdrawn into the body of the valve 100 with the piston. Since the outer diameter of the skirt 1f is less than the outer diameter of the base 1b of the piston 1, fluid will flow about the external surface of the skirt 1f and through the apertures 1i to the interior of the valve 100 and thence via the exit side 11 of the valve 100 to downstream processing.

Figure 2A:
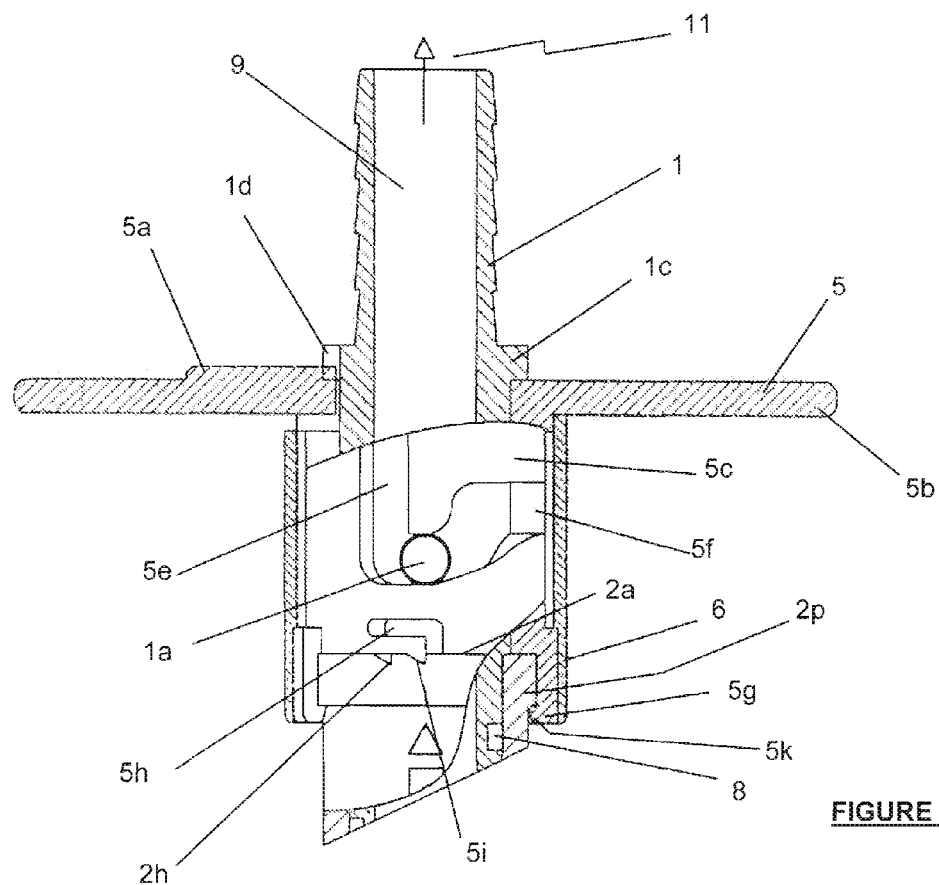
FIGS. 2a and 2b are respectively enlarged side sectional and plan views of the actuation means of the valve of FIG. 1b prior to actuation.
Figure 2B:
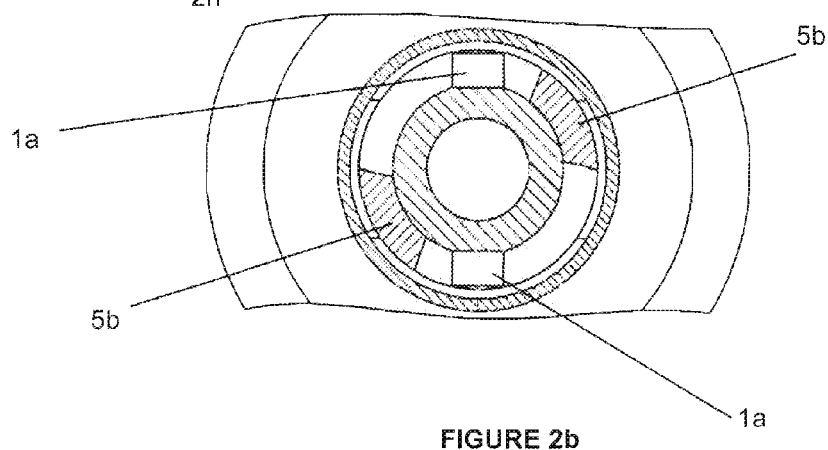
Figure 2C:
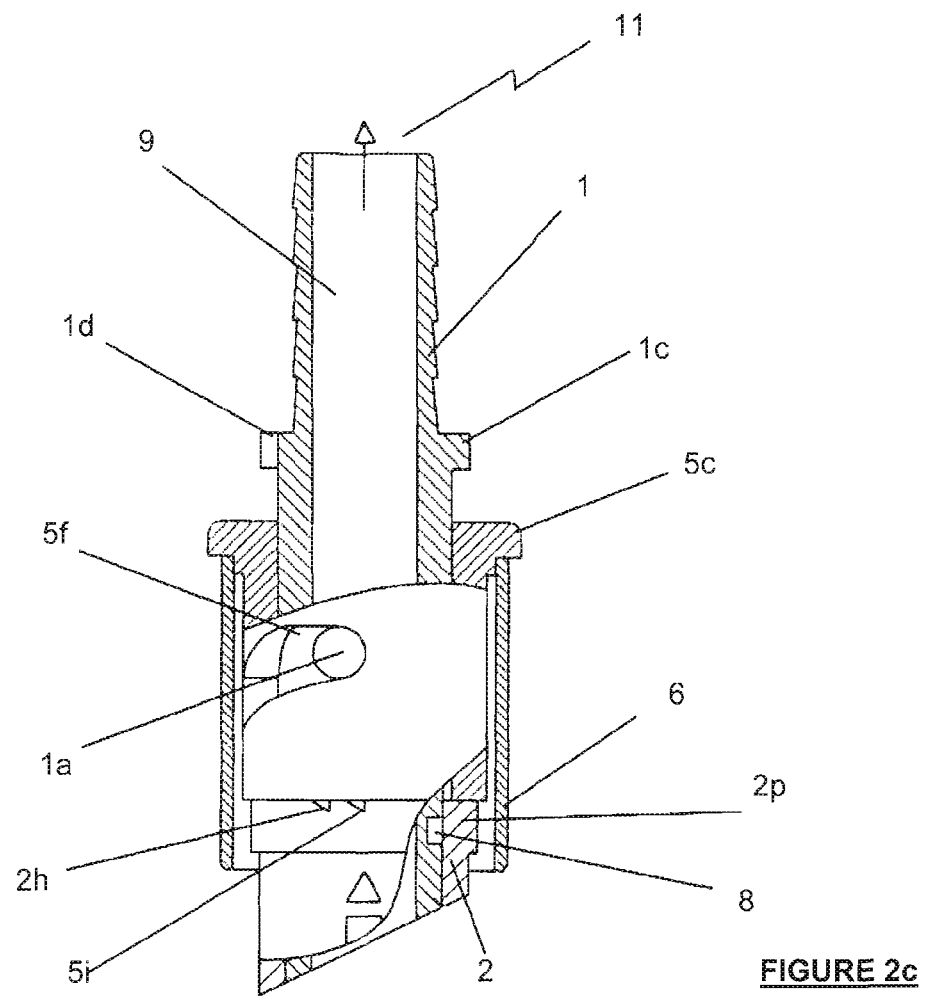
FIGS. 2c and 2d are respectively enlarged side sectional and plan views of the actuation means of the valve of FIG. 1b after activation.

FIGS. 2a and 2c are enlarged side section views of the actuator 5 and locking mechanism 5a of valve 100 prior to and after activation respectively. The actuator 5 is connected to housing 2 by a snap-lock mechanism 5g which comprises a pair of resiliently inwardly biased connectors 5k which snap over the collar 2p of the housing 2. The actuator 5 and piston 1 are connected by means of a cam mechanism 5c, comprising a pair of opposing outwardly projecting pins 1a on piston 1 which travel in a pair of shaped slots 5d on actuator 5. Each of the shaped slots 5d has a first section 5e which is substantially parallel to the longitudinal axis of the piston and a curved cam section 5f with a first region substantially perpendicular to the longitudinal axis of the piston and a second region curving more sharply toward the handle 5b for lifting the piston within the housing. The shaped slots 5d are positioned diametrically opposite one another.

On assembly, and as best illustrated in FIGS. 1a, 1b, 1e, 1i, 1j, 1k and 9, the piston 1 is inserted through a top opening 51 on the actuator 5, the skirt 1k at the base 1b of the piston leading, with the pins 1a fitting through recesses 5m on the opening. The pins 1a pass through the recesses 5m and engage in the first sections 5e of the profile slots 5d. The distance by which the piston 1 can be inserted into the actuator 5 is determined by the length of the first section 5e. Once the pins 1a engage with the bottom of the first section Se, the radially projecting flange 1c of the piston 1 abuts the underside of handle 5b of actuator 5. The piston 1 and actuator 5 are then rotated relative to one another so that the tongue 5j of the locking mechanism 5a engages in the recess 1d on flange 1c, thereby preventing further rotation. This position comprised the state of the valve in which it is supplied closed and ready for use, herein referred to as the "ready state".

In use and in order to open the valve 100, the locking mechanism 5a is released as described above by depressing the tongue 5j. Once the locking mechanism 5a is fully released, handle 5b can be rotated. The rotation of actor 5 causes pins 1a to move out of the lock position shown in FIGS. 1a and 2a and into and along the curved cam section 5f. The transition from the closed, ready for use, state to the open, deployed, state will be described in more detail below.

The curved cam section 5f has two regions. Of these, the first is substantially perpendicular to the longitudinal of the piston 1 but has a gentle curve toward the handle 5b. Therefore, as the rotation of the handle 5b proceeds, the pins 1a move along this perpendicular region causing the piston 1 to travel along its longitudinal axis, thereby causing the seal 2a connected to the opposite end of the piston 1 to shear and break at junction 2b. The gentle curve assists in the tearing away of the seal as the piston travels along its longitudinal axis it causes the piston to lift gently away from the flange 21 of the sleeve portion 2i as rotation continues. In the next stage of opening the valve 100, the now broken-away seal 2a is moved away from the flange 21 by withdrawing it together with the piston 1. This is achieved by continued rotation of the handle 5b which moves the pins 1a into the following, more steeply curved path of the cam region of the curved cam section 5f. As the pins 1a move along this path the piston 1 travels along its longitudinal axis in a direction away from the flange portion 2j. At the end of the rotation of the handle, the seal 2a has moved away from its position blocking the entry side 10 and fluid communication between the vessel 4 and the valve 100 is achieved as described above.

Figure 2D:
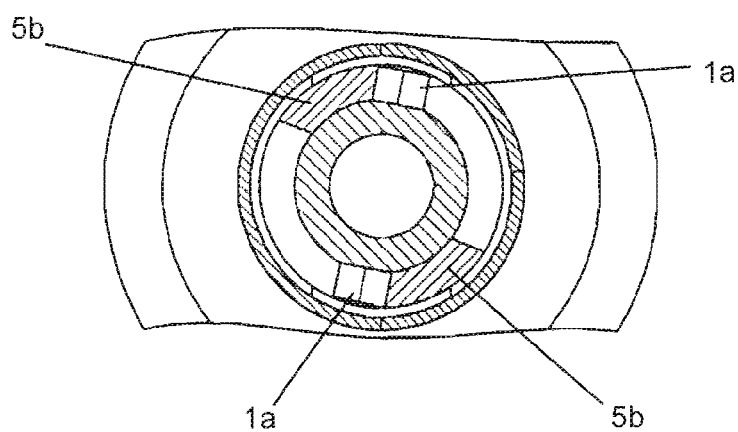

FIGS. 2b and 2d are plan views of the position of the actuator 5 before and after actuation of the valve 100 respectively, that is to say, with the valve closed end open.

As described above the substantially perpendicular region of the curved cam section 5f is in fact not perfectly straight, but is ideally formed with a gradual slope to assist breakage of the seal 2a. In one preferred arrangement, the initial rotation of the handle 5b from 0° to about 56° accomplishes breakage of the seal 2a, whilst the sharply sloping cam region is from about 56° to about 80°.

Figure 1D:
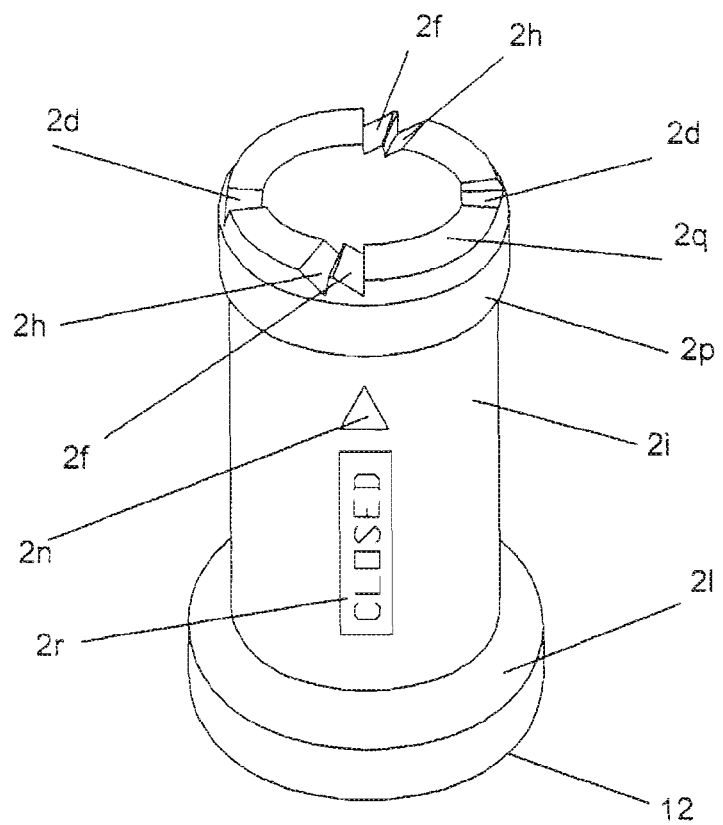
Figure 1E:
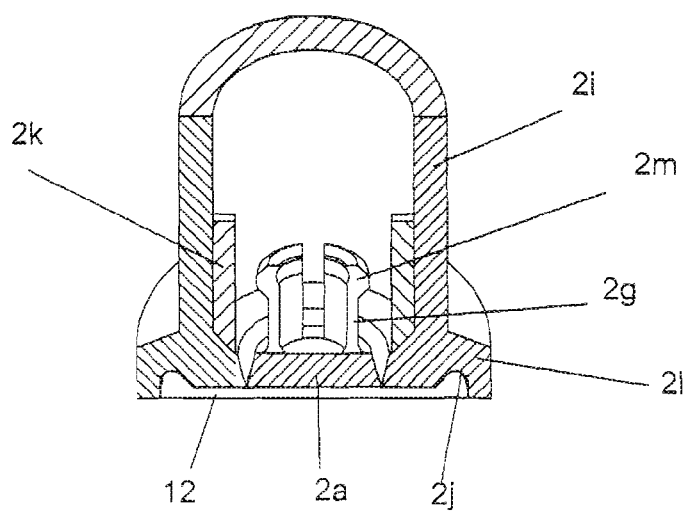
FIG. 1e is a perspective cross section view of the lower half of the housing of FIG. 1e.
Figure 1F:
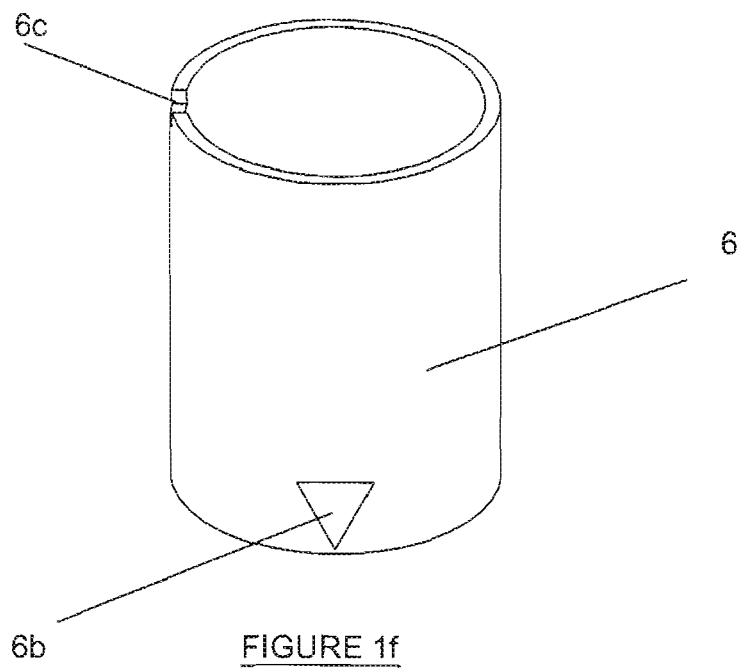
FIGS. 1f and 1g are respectively perspective and perspective cross-section views of a cover.
Figure 1G:
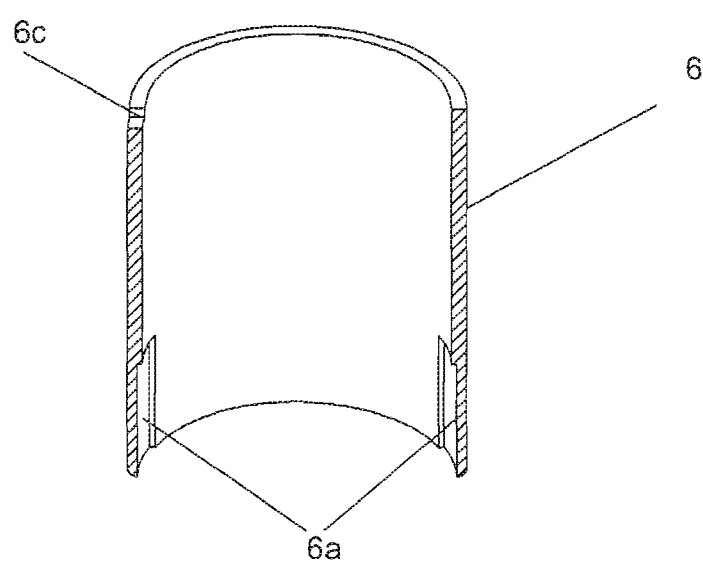
Figure 1J:
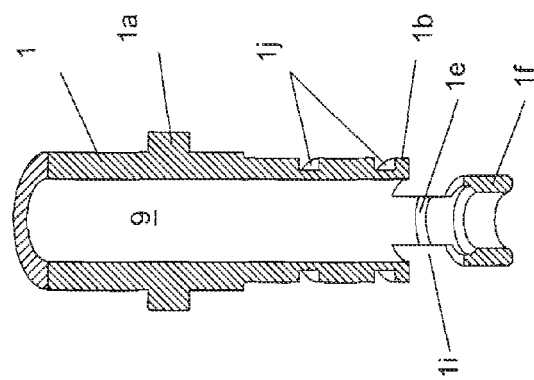
FIGS. 1h and 1j are respectively perspective and persoective cross-section views of the piston of the first embodiment of the valve and FIG. 1i is a perspective view of the piston rotated about its longitudinal axis by 90° compared to that of FIG. 1h and with a modified exit end.
Figure 1I:
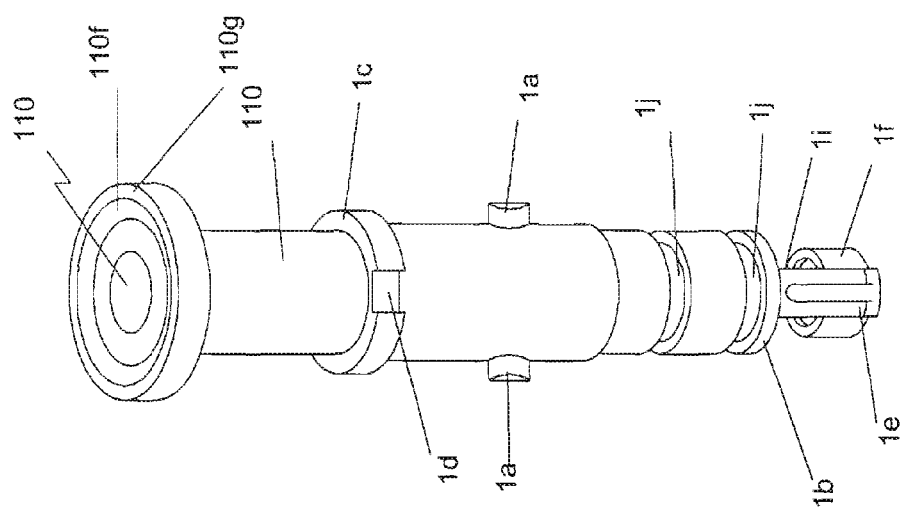
Figure 1H:
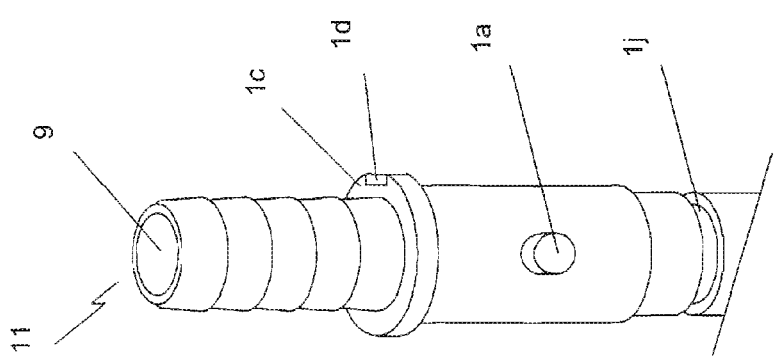
Figure 1K:
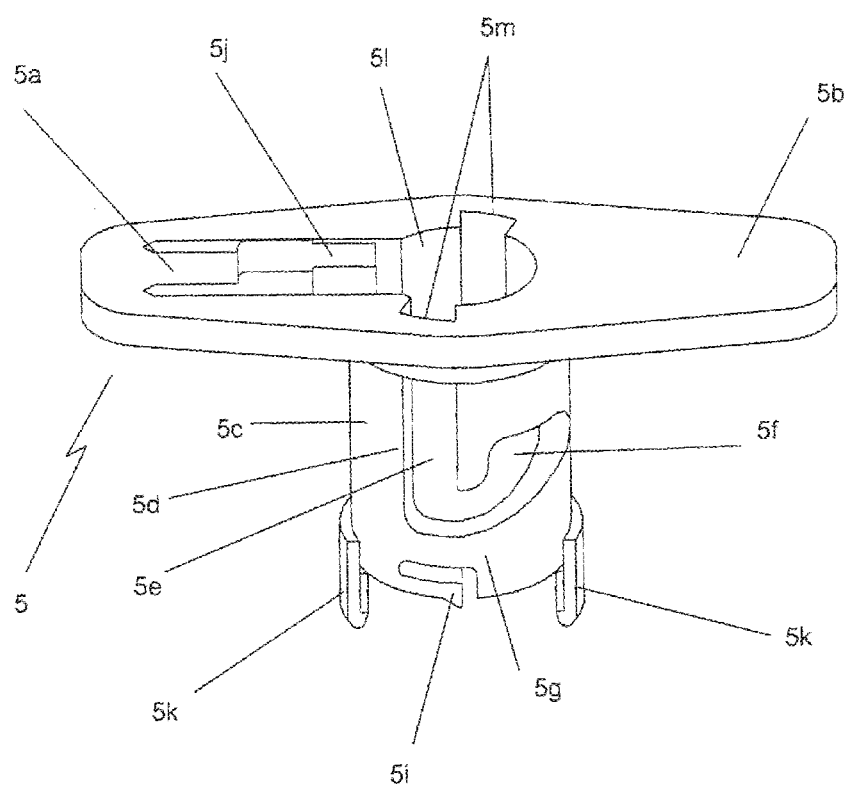
FIG. 1k is a perspective view of the actuator of the first embodiment of the valve.

Referring now to FIGS. 1a, 1d and 1k, the counter rotation of handle 5b is prevented by stop means comprising a pair of opposing resilient teeth 5i on the actuator 5 remote the handle 5b (only one tooth is visible in the drawings) and two sets of notches 2d, 2f and 2h on the upper surface 2q of the collar 2p of the housing 2. On assembly of the valve 100, the piston and actuator 5 are in a relatively locked position and rotation of the actuator 5 is prevented. The teeth 5i engage in this state with first notches 2f. There are markings 2n, 2r, 6b provided on the outer surface of the cover 6 and housing 5 (see FIGS. 1d and 1f) which are arranged so that when they are aligned, they indicate that the valve 100 is closed. Valve 100 is assembled and presented to the user in this ready, closed state, with each tooth 5i engaged in a notch 2f. When the valve is in this state, the tongue 5j of actuator 5 is engaged with recess 1d of the piston and the piston pins 1a are engaged at the base of first section 5a of the slots 5d. In this position, the valve is closed and the tips of the arrowheads 2n of housing 2 and 6b of cover 6 face each other to indicate that the valve is closed. In the first stage of operating the valve, tongue 5j is depressed as described above to release it from recess 1d, thereby enabling handle 5b to rotate, bringing teeth 5i out of notches 2f and into notches 2h. In this intermediate position the valve is still closed, since although pins 1a have displaced slightly into the first region of the cam section 5f of the slots 5d, they have not moved sufficiently to begin to tear open seal 2a. Nevertheless, the arrow tips 2n and 6b will now have moved apart by a distance equal to the distance between the bases of notches 2f and 2h, and this gives an indication to the user that it should not be assumed that the seal is intact, but that it should be checked before continuing. Since the teeth 5i are engaged in notches 2h in the intermediate state, the valve will remain in this state until the user turns the handle sufficiently forcefully to pull the teeth 5i out of notches 2h. The next step opens the valve. It is effected by further rotating handle 5b to cause the teeth 5i to ride over and out of notches 2h and travel into notches 2d. When notches 2d are reached, the valve is fully open, since the pins 1a have travelled to the end of cam section 5f, tearing open the seal and lifting is free of the open first end of the valve.

The notches 2d, 2f and 2h have a sloped side that enables the teeth 5i to easily slide out of each notch, 2d, 2f and 2h in one direction only. Movement in the reverse direction is prevented as the tooth abuts the sheer face of the notch and cannot travel over it.

Referring to FIGS. 1h and 1i, there are shown two possible variations of the exit side 11, 110 of the piston 1. In FIG. 1h, this end 11 is formed with external ribbing to enable it to be connected to another enclosure, be it vessel or line. In the FIG. 1i modification, the exit end 110 is formed with a coupling flange 110f, 110g to enable it to be connected to a mating surface, for example to a surface of another vessel. This is an arrangement comparable to the coupling flange 2b of the housing 2.

As best seen in FIGS. 1f and 1g, the cover 6 is formed as a sleeve sized to cover the exteriors of the housing and cam mechanism 5c of actuator 5. A pair of opposed open slots 6a are provided at the base of cover 6. When the valve is assembled, these slots supply a clearance for the connectors 5k which snap over the collar 2p of the housing. The slots 6a also provide a sufficient flexibility to the cover so that finger pressure exerted on the base of the cover at the points which are 90 degrees displaced from the slots 6a enables the cover to flare sufficiently to assist its release from the housing, subject to the material of the valve being capable of sufficient deformation to allow this. Recess 6c on the upper end of the cover 6 provides a clearance for the tongue 5j to be depressed into when that tongue is released from the piston recess 1d to allow the valve to be opened.

FIGS. 3a and 3b are side section views and plan views of the seal 2a of valve 100 before opening. FIGS. 3c and 3d are corresponding views after opening. The seal 2a is connected to the piston 1 using the snap-lock described above. This configuration enables the seal 2a to withstand pressures which are a multiple of the normal pressure of a steam sterilising fluid load without rupturing seal 2a at the junction 2b.

FIGS. 4a and 4b show a second embodiment of the valve 200 of the invention. Valve 200 operates as previously described in relation to the first embodiment. In this case valve 200 is coupled to an opening 40c of a separate vessel or pipe 40. The coupling surfaces 212, 413 of both the valve 200 and the opening 40c have a projecting rim 20a and 40a respectively encircling the outer edge of the surfaces. Each surface also has a groove 2j and 4a respectively encircling the circumference of the surface intermediate the seal 2a and the projecting rim. A washer 3 is placed between the two surfaces to provide a seal between them and the washer has complementary ring formations 30a sized and shaped to fit within the grooves in the coupling surfaces.

Figures 5A, 5B:
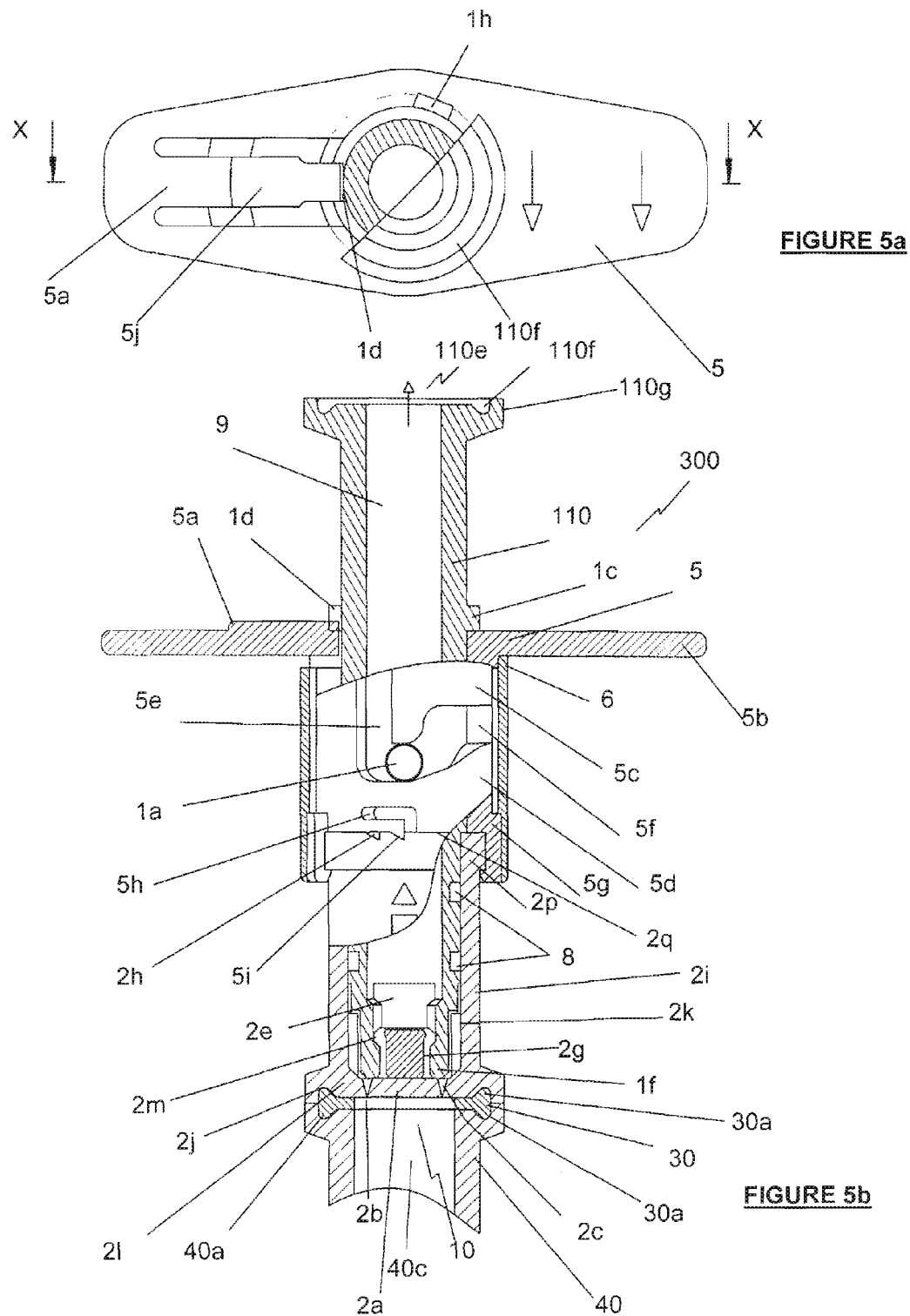
FIG. 5a is a plan view of a third embodiment of a single-use valve according to the invention.
FIG. 5b is a side sectional view of the valve of FIG. 5a along the line X-X.

FIGS. 5a and 5b are views of a third embodiment of the valve 300 of the invention, which is a modification of the second embodiment. Valve 300 is adapted to connect at its exit side to an opening on a pipe or vessel in similar fashion to the connection at the entry side. The exit side of the piston 110e includes a connecting surface with a projecting rim 110g encircling its outer edge and a groove 110f to receive the washer in the same manner as described in relation to the entry side of the valve.

Figure 6:
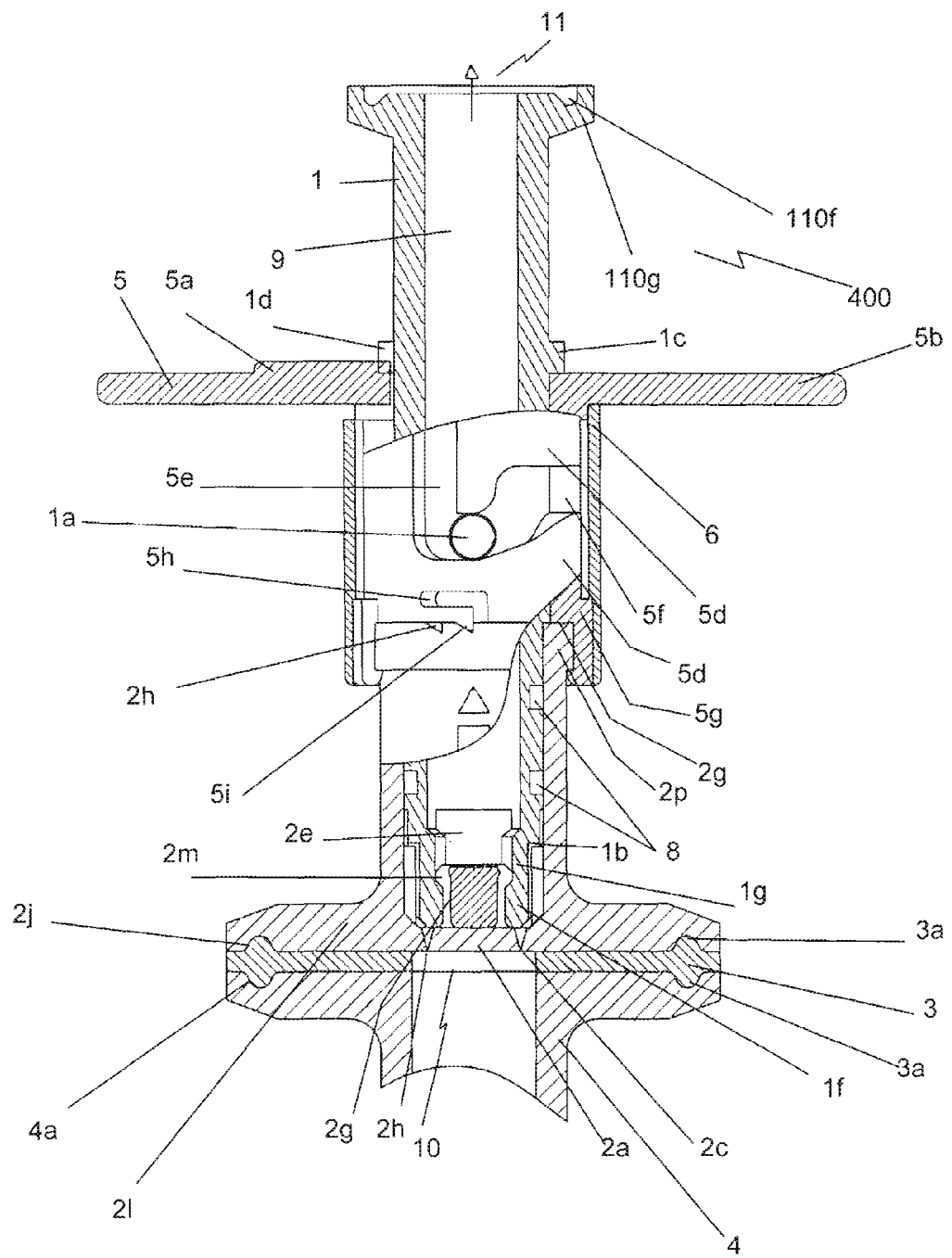
FIG. 6 is a side sectional view of a fourth embodiment of a single-use valve according to the invention.

There is shown in FIG. 6a a fourth embodiment of a valve 400, which is a modification of the first valve embodiment. Valve 400 is modified to connect at it's exit side to an opening on a pipe or vessel in a similar fashion to the third embodiment of the valve.

Figure 7:
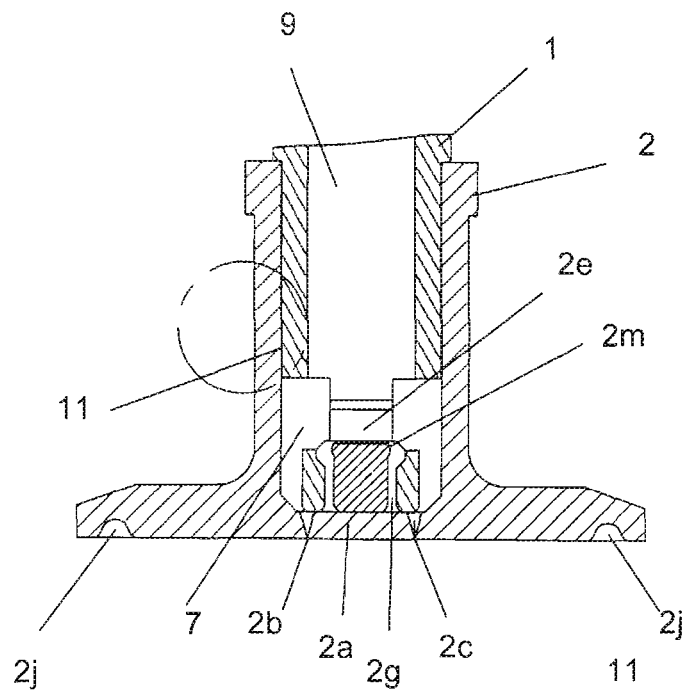
FIG. 7 is a side sectional view of the seal portion of the valve according to the invention prior to activation.
Figure 7A:
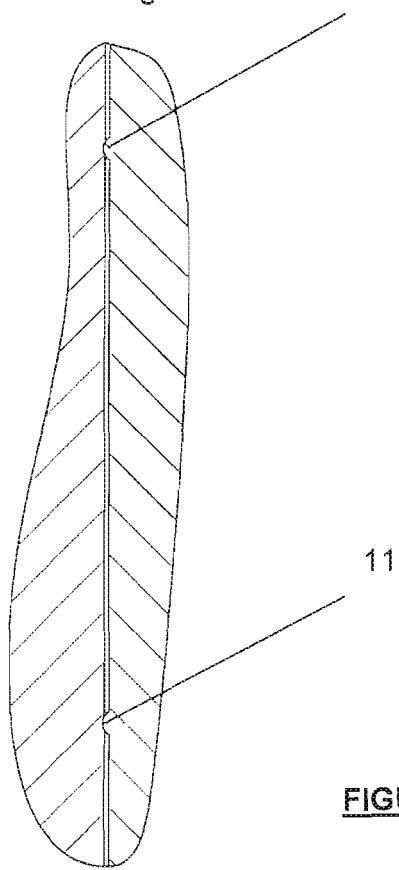
FIG. 7a is an enlarged view of the ringed portion of FIG. 7.

FIG. 7 is a side section view of a variant seal section of a valve prior to activation. FIG. 7a is an enlarged view of the ringed portion of FIG. 7. These figures show a double mating seal edge 11 as an alternative, effective seal between the piston 1 and the housing 2. The double seal edges 11 are formed during the moulding process of the individual components of the valve. The seal edges 11 are formed as radial projections encircling the external surface of the piston 1. The projections 11 provide an effective seal when the piston 1 is inserted into the housing 2. The projections also provide resistance for the piston 1 when it moves preventing overshooting and other associated problems.

FIGS. 8a to 8i are a series of side sectional views of different openings 301 to 309 to which a valve according to the invention can be coupled. Also shown are different types and sizes of washers 301a to 309a which can also be used to facilitate sealing between the valve and the openings 301b to 309b. Many other shapes and configurations of the valve, opening and washer are possible within the scope of the invention.

Referring now to FIGS. 9a to 9g, there are shown the steps taken in the assembly of the valve 100. The O-rings 8 are placed in recesses provided on the external surface of the piston 1. The piston 1 is then inserted into the actuator 5 (step 1001), The piston 1 is rotated within the actuator 5 to allow the locking mechanism (not shown) engage with the recess in the projecting flange of the piston (step 1002). Simultaneously the cover 6 is placed over the housing 2 (step 1003). The piston 1 and actuator 5 combination are inserted into the assembled housing 2 / cover 6 (step 1005), so that the housing 2 and actuator 5 engage by means of the snap-lock mechanism and the seal (not shown) and piston 1 also connect by means of their snap-lock mechanism (step 1006). Once the individual components are connected to each other the cover 6 is pushed up over the housing 2 to cover the cam mechanism on the actuator 5 (step 1007). A plug insert 2e is inserted into the piston 100 from the exit side down to the entry side to engage between the fingers 2g (not shown) connecting the seal and the piston 1 (step 1008). The closed valve can then be bagged or packaged in some convenient way and sterilised. Optionally, other components useful in effecting a transfer may be packaged with the valve.

Figure 10A:
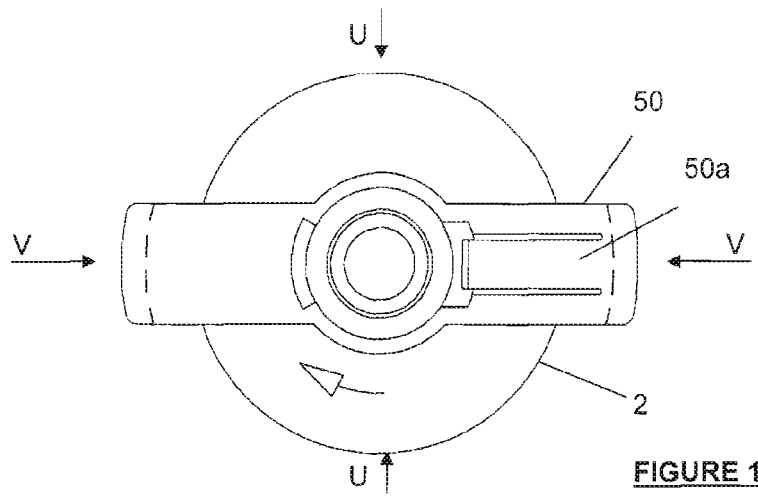
FIG. 10a is a plan view of a fifth embodiment of a single use valve according to the invention.
Figure 10B:
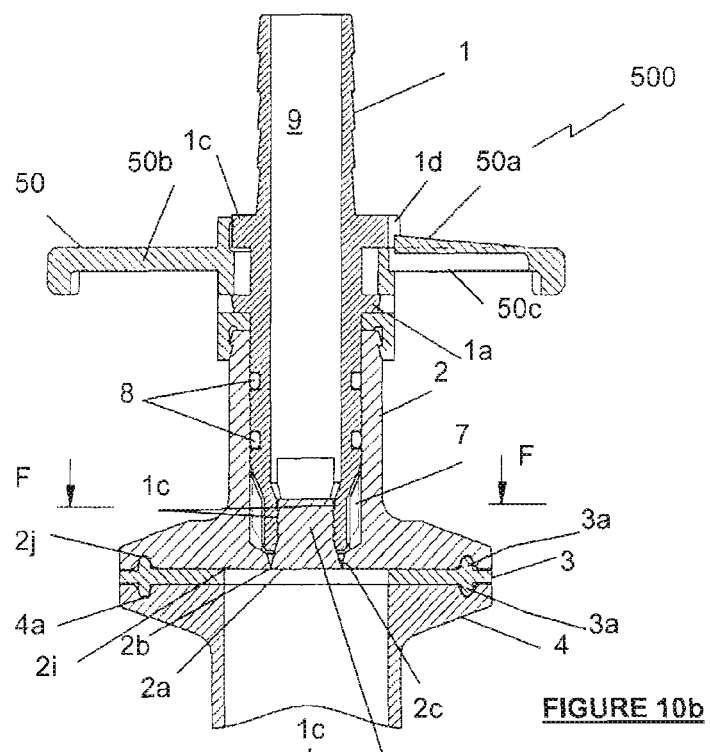
FIG. 10b is a side sectional view of the valve of FIG. 10a along the line V-V.
Figure 10C:
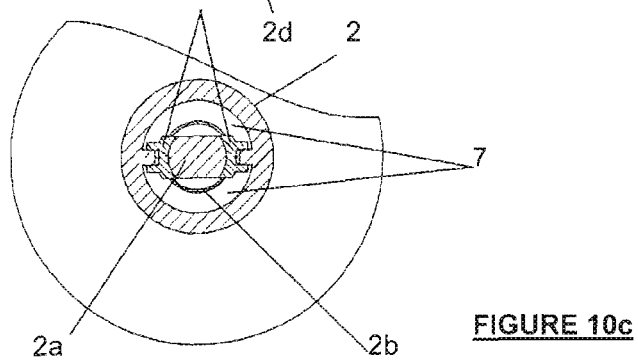
FIG. 10c is a sectional view of the valve along the line F-F of FIG. 10b.

FIGS. 10a, 10b and 10c are a plan view, a side section view and a sectional view of a fifth embodiment of a single use valve 500 according to the invention. Valve 500 operates in the same manner as the previous embodiments of the valve, however the way in which the piston 1 is connected to the seal 2a is different. In this embodiment, the piston 1 and seal 2a are connected by means of a saw-tooth configuration 1c. The saw tooth fit also enables the seal 2a withstand pressures which are a multiple of the normal pressure of a sterilising fluid load without rupturing seal 2a at the junction 2b.

Figure 11:
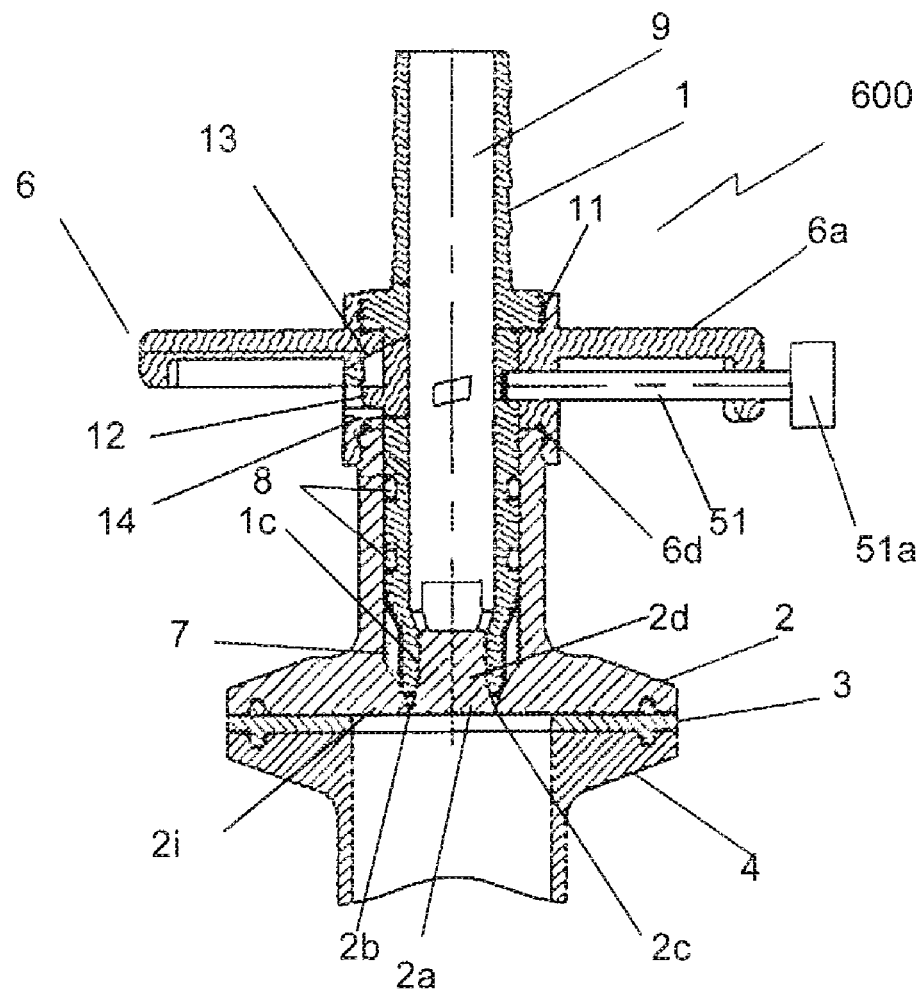
FIG. 11 is a sectional view of a sixth embodiment of a single use valve according to the invention.

FIG. 11 is a side section view of a sixth embodiment of a single use valve 600. The actuator 5 has a locking mechanism 51, which differ to that of the other embodiments of the value. Actuator 5 is connected to the housing 2 by means of a snap-lock mechanism 6d. The piston 1 is connected to the actuator 5 by means of a screw thread mechanism 11, where the interior surface of the actuator 5 and the exterior surface of the piston 1 are provided with mutually engageable screw threads.

Actuator 5 is biased to rotate and the locking mechanism 51 comprises a locking pin 51a that inserts into piston 1 through actuator 5 thereby preventing rotation of actuator 5 against the bias. When the locking pin 51a is withdrawn, actuator 5 is free to rotate under the bias and rotates a number of degrees which is an insufficient distance to rupture the seal 2a but which is sufficient to prevent reinsertion of the locking pin 51a. Thus if there is no locking pin 51a present, this provides a warning to a user that the valve may be compromised.

Once the pin is withdrawn, the actuator 5 is rotated further to rupture seal 2a. The seal 2a is connected to the piston 1 by means of the saw-tooth configuration 1c described above in connection with FIGS. 10a to 10c. As the actuator 5 is rotated, the piston 1 moves further from the entry side of the valve 600 rupturing the seal 2a and enabling fluid to gain entry to the valve 600. The distance the seal 2a travels from the entry side of the valve 600 is determined by the degree of rotation of the actuator 5.

A limiting mechanism for preventing the piston from travelling too far in either direction is also provided. The exterior surface of piston 1 has a detent 12 remote the entry point of the locking pin 5a. Detent 12 comes into abutment with surface 14 when piston 1 travels towards the sealed entry side of valve 101 preventing further movement in that direction. Similarly detent 12 abuts surface 13 when piston 1 travels away from the sealed entry side of valve 101 preventing further movement in the direction away from the sealed entry side of valve 101.

Figure 12A:
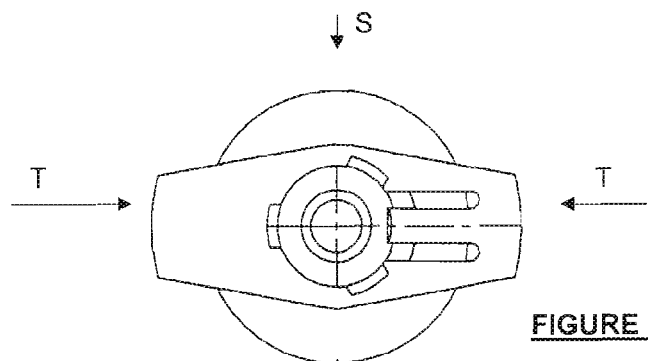
FIG. 12a is a plan view of a seventh embodiment of a valve according to the invention.
Figure 12B:
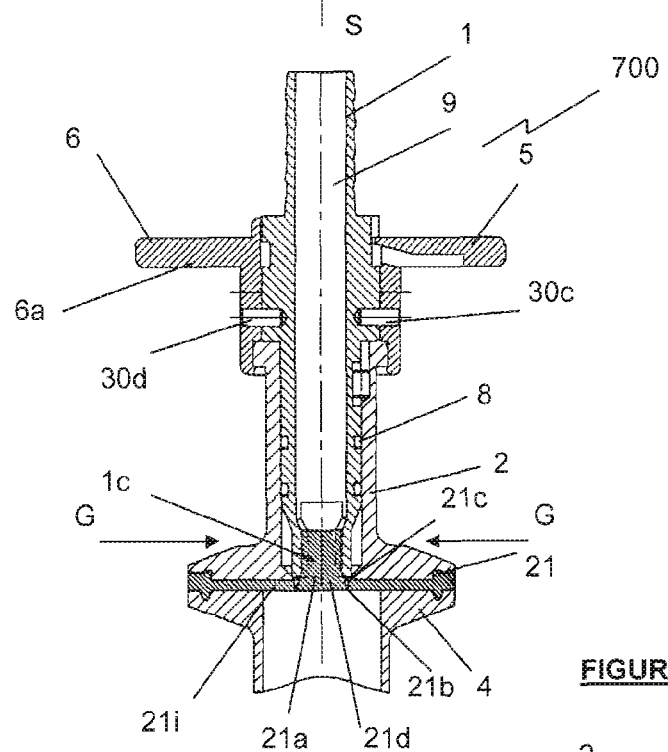
FIG. 12b is a side sectional view of the valve of FIG. 12a along the line T-T.
Figure 12C:
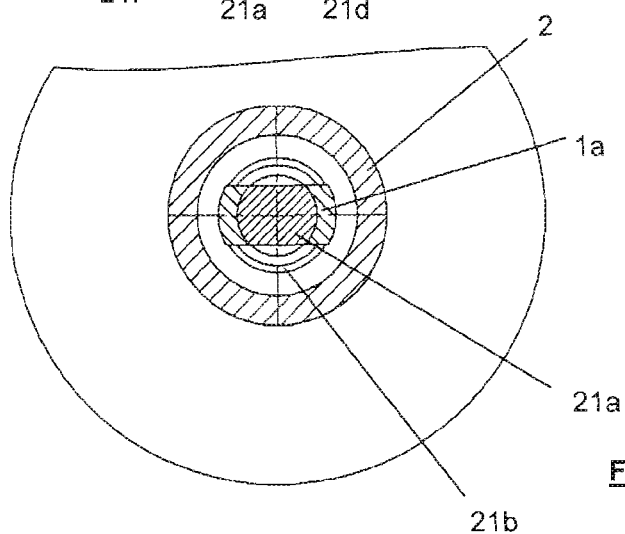
FIG. 12c is a sectional view of the valve along the line F-F of FIG. 10b.

Referring now to FIGS. 12a, 12b and 12c, there is shown an embodiment of a multi-use valve 700 according to the invention. The seal 21a is provided as a replacable attachment. Seal 21a is secured to the valve as follows; seal 21a attaches to piston 1 by means of a saw-tooth configuration 1a and a collar portion (not shown) is clipped in place using clip-on mechanism 21. The collar portion is further secured in position when attached to opening 4. Seal 21a also acts as a washer between the valve 700 and opening 4.

In use valve 700 operates in the same way as the single-use valves 100 to 600 respectively. The actuator 5 and locking mechanism 5a are provided as a clip release mechanism as described for single-use valve 100. Once the locking mechanism 5a is released, the actuator 5 is free to rotate. The piston 1 travels in a direction away from the sealed entry side of the valve 700 by means of pins 30c and 30d which follow profiled slots (not shown) as for single-use valve 100. As piston 1 travels in a direction away from the sealed entry side of the valve 700, the seal 21a ruptures at fracture line 21b and moves with the piston 1 enabling fluid to gain entry to the valve 700.

Figure 13:
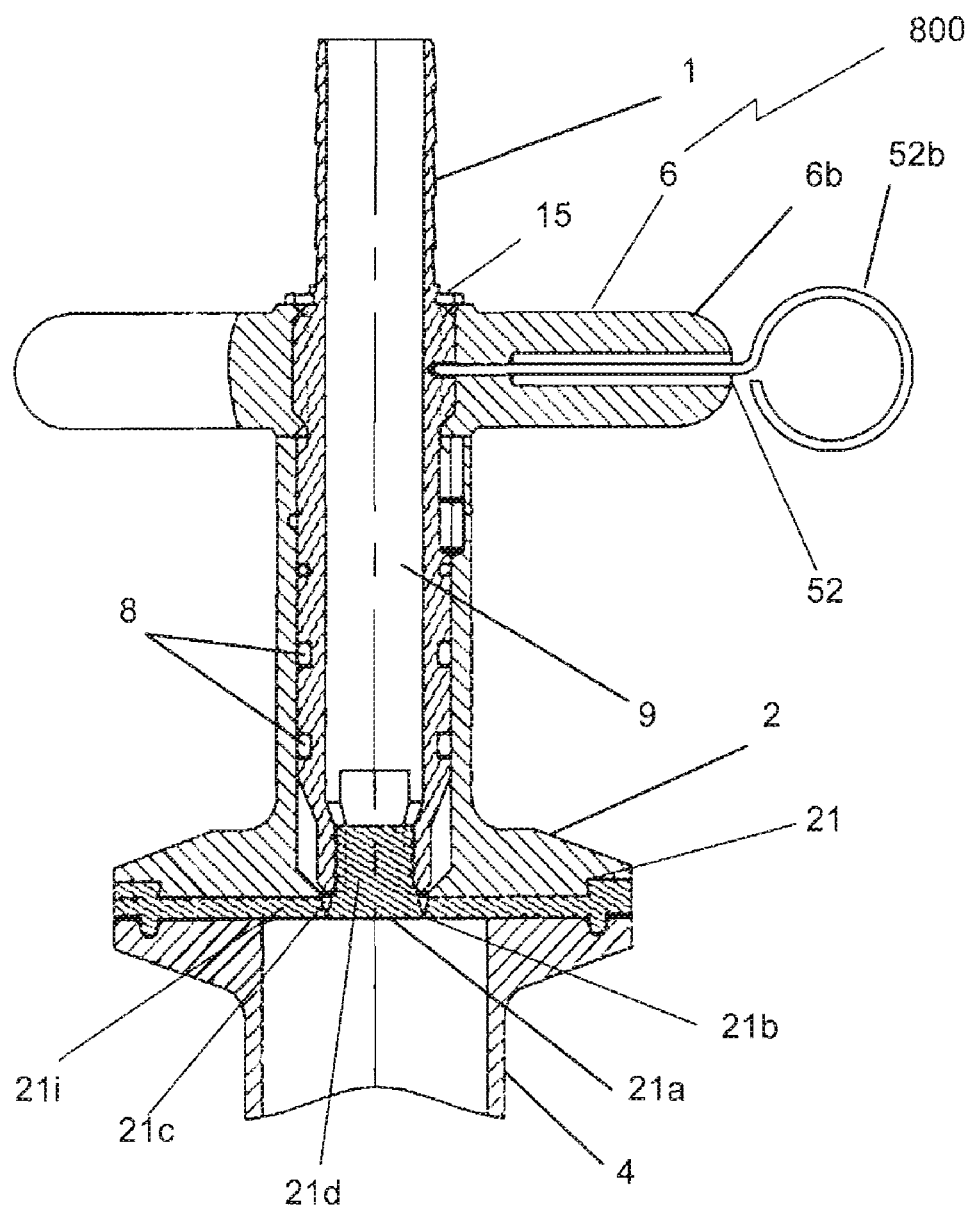
FIG. 13 is a side sectional view of a eighth embodiment of a valve according to the invention.

FIG. 13 is a further embodiment of a multi-use valve 800 according to the invention connected to an opening 4. The actuator 5 and locking mechanism 52 of valve 800 differ from that of valve 700 of FIG. 12b. Actuator 5 is attached to piston 1 remote the sealed entry side of the valve 800 by means of a screw thread mechanism. The inner surface of actuator 5 has a first screw thread, the exterior surface of piston 1 has a second screw thread and both screw threads are mutually engaging. The actuator 5 is also secured to housing 2 by means of securing fitting 15. Securing fitting 15 is attached to the actuator 5 and piston 1 remote the housing 2 forcing the actuator 5 into contact with the housing 2 at the surface remote the securing fitting 15.

Locking mechanism 52 is provided as a locking pin 52b that inserts into piston 1 through handle 6b of actuator 5. Locking pin 5b is removed completely to operate valve 103. When locking pin 5b is removed, actuator 5 is free to rotate.

As actuator 5 rotates piston 1 is forced to travel in a direction away from the sealed entry side of valve 800. The seal 21a travels with piston 1 causing seal 21a to rupture at fracture line 21b enabling fluid gain entry to the valve 800.

The piston 1, housing 2, actuator 5 and locking mechanism 5 of multi-use valves are generally manufactured from a heavy duty durable material such as stainless steel. Alternative materials can also be used. Sealing O-rings 8 are used as the piston seal when the piston 1 and housing 2 are formed from stainless steel. The seal 21a of a multi-use valve can be made from any suitable material known to a person skilled in the art including plastics, foil and rubber or rubbery-type materials including flexible and inflexible materials. The seal 21a is replaced when required by removing the old ruptured seal and inserting a new seal into position, snapping it securely in place in the saw-tooth configuration between the piston 1 and seal 21a. Any one seal 21a may be used more than once in the multi-use valve, with appropriate cleaning and resterilisation. However it is not recommended to use a seal more than five times in order to maintain the integrity of the system. Alternatively the seal 21a can be replaced after each use once the seal is broken.

One example of how the valve of the invention may be used in practice will now be described. In this example, a first vessel is to be connected to a second vessel by means of a tubing. The tubing is provided with a valve according to the invention at each of its ends. The tubing with the valves attached at either end is placed in a bag and sterilised, for example by steam, gas, radiation or any other suitable means. In a first step, the bag is opened and one of the valves is removed, thereby exposing the external sealing surface of that valve to environmental contamination. This valve is coupled to the first vessel and the first vessel is then steam sterilised, thereby also resterilising the exposed face of the valve. This first vessel with attached tubing is next transferred to the site of the second vessel. There, the valve on the opposite end of the tubing is released from the bag and connected to the second vessel in like manner as described in relation to the first valve and first vessel. The second vessel and attached valve are then steam sterilised. Now, both valves may be opened providing a sterile fluid path between the first and second vessels.

In operation of the valve of the invention, the valve is pre-sterilised, for example by gas, gamma ray or steam sterilisation, prior to use. At this stage, it is in its closed position. Once sterilised, the valve can be connected to any desired opening of a pipe or vessel. In connecting the valve to the opening the external surfaces of the valve including the exterior sealed entry side of the valve is exposed to the atmosphere thus sterility is compromised. Once the valve is connected, the vessel or pipe to which it is attached is sterilised, enabling the external connecting surface of the valve to be resterilised. Once the connecting surface of the valve has been resterilised the valve can be opened when required.

The valve or any of its parts may be fabricated from any suitable material including plastics materials (such as polypropylene and the like) and metals or ceramics. Plastics are particularly preferred for the single use valve.

Whilst the valve has been specifically described with reference to a seal which is torn away from a sealing interface and withdrawn into the body of the valve, it will be appreciated that other arrangements will be possible within the scope of the invention. For example, the piston may be arranged to drive the seal out of the valve to unblock the fluid passageway. Likewise, the piston may be arranged to rupture or break the seal by cutting it open and bending the torn parts out of the fluid path. Many different forms of seal will be possible within the scope of the invention, including thin or thick membranes, foils, flexible and inflexible materials.

It will be understood that the invention is not limited to specific details described herein which are given by way of example only and that various modifications and alterations are possible without departing from the scope of the invention, as defined in the appended claims.

The invention claimed is:

1. A valve comprising a body having first and second open ends and a passageway for fluid between the ends, said first end including a coupling means for sealingly connecting said body about an opening of an external device and a seal blocking said open area of said first end which in use is placeable in register with said opening of said external device, said valve further including a seal displacement means movable within said body so as to interrupt said seal permitting fluid to pass along the passageway between said ends, said coupling means and seal presenting an external sterilisable mating surface for sealingly mating with a mating surface about said opening in said external device;

in which said displacement means comprises a means for rupturing said seal so as to allow fluid communication between said interiors of said body and said external device;

in which said rupturing means is arranged to break said seal by gripping it through mutually engageable gripping means and withdrawing said seal or a portion of it away from said mating surface;

in which said mutually engageable gripping means are provided on said seal and rupturing means and said rupturing means is moveable within said body of said valve in a direction from said first end toward said second end so that on movement of said rupturing means, said gripped seal is broken free from said coupling means and withdrawn into the interior of said body; and in which said rupturing means comprises a hollow piston which has an open end comprising said second open end of said valve body.

2. A valve as claimed in claim 1, in which said seal is formed integrally with said coupling means at said sterilisable external surface.

3. A valve as claimed in claim 2, in which a junction is provided between said coupling means and said seal and comprises at least one weakened fracture line so that when said rupturing means moves within said body it breaks said seal along at least a portion of said at least one fracture line.

4. A valve as claimed in claim 3, in which said junction or fracture line comprises an area of reduced thickness of said mating surface.

5. A valve as claimed in claim 4, in which said fracture line is endless and encloses said seal.

6. A valve as claimed in claim 3, in which said fracture line is in the shape of a circle and said seal is disc shaped, and when said rapturing means is moved, it causes said disc shaped seal to be displaced from its position blocking said opening of said first end.

7. A valve as claimed in claim 1, in which said coupling means includes an upstanding cylindrical portion within which said piston moves and sealing means are provided between said piston and said cylindrical portion.

8. A valve as claimed in claim 1, in which one or more apertures are provided in a wall of said piston adjacent said seal so that fluid may pass between said interior of said piston and said first end via the or each aperture.

9. A valve as claimed in claim 1, in which an actuation means is provided for moving said piston between a ready state in which said seal is intact and said valve is closed and a deployed state in which said seal is broken and moved with said piston away from the mating surface so that said valve is open.

10. A valve as claimed in claim 9, in which the actuation means include a handle operable by a user and a collar portion connected to the cylindrical portion of the coupling means and to the piston for effecting relative movement between the cylindrical portion and the piston on operation of the handle.

11. A valve as claimed in claim 9, in which said piston and ripped seal are withdrawn into said cylindrical portion of said coupling means as said actuator moves said piston from said ready state to said deployed state.

12. A valve as claimed in claim 9, in which said actuation means includes a safety lock means for preventing undesired movement of said piston.

13. A valve as claimed in claim 12, in which said safety lock means comprises a tongue releaseably engageable with said piston for preventing movement from said ready state to said deployed state.

14. A valve as claimed in claim 9, including stop means for preventing said actuator from moving in a reverse direction which would return said value from said deployed state to said ready state.

15. A valve as claimed in claim 9, including visible or tactile indication means for indicating to a user said valve's position between its ready and deployed states.

16. A valve as claimed in claim 1, in which the second end of said body includes means for attaching said second end to a downstream process area.

17. A valve as in claim 1, comprising a single-use valve.

18. A valve comprising a body having first and second open ends and a passageway for fluid between the ends, said first end including a coupling means for sealingly connecting said body about an opening of an external device and a seal blocking said open area of said first end which in use is placeable in register with said opening of said external device, said valve further including a seal displacement means movable within said body so as to interrupt said seal permitting fluid to pass along the passageway between said ends, said coupling means and seal presenting an external sterilisable mating surface for sealingly mating with a mating surface about said opening in said external device;

in which said displacement means comprises a means for rupturing said seal so as to allow fluid communication between said interiors of said body and said external device;

in which said rupturing means is arranged to break said seal by gripping it through mutually engageable gripping means and withdrawing said seal or a portion of it away from said mating surface; and in which said gripping means include at least one finger element projecting into said valve interior from said inner surface of said seal and a receiver element provided on said rupturing means for securely receiving and retaining said finger element.

19. A valve comprising:

a body having first and second open ends; and a passageway for fluid between the ends, the first end including a coupling means for sealingly connecting the body about an opening of an external device and a seal blocking the open area of the first end which in use is placeable in register with the opening of the external device, the valve further including a cam and follower arrangement for moving a seal displacement means movable within the body comprising an actuator, positioned concentrically about said body and rotatable about the axis of said body and having a pair of shaped slots and a piston having a pair of opposing outwardly projecting pins wherein each of said outwardly projecting pins are cooperatively engaged within said shaped slots and wherein each of said shaped slots has a first section that is substantially parallel to the longitudinal axis of said piston and a second section that is curved in a direction substantially perpendicular to the longitudinal axis of said piston.

20. A valve as claimed in claim 19, wherein said first section contacts said pins from 0 to 56 degrees rotation of said actuator and said second section contacts said pins from 56 to 80 degrees rotation of said actuator.

21. A valve as claimed in claim 19 in which said seal displacement means is movable between a ready state in which said seal is intact and the valve is closed and a deployed sate in which said seal is broken and moved with the seal displacement means away from the mating surface so that the valve is open.

22. A valve as claimed in claim 19 in which the seal displacement means and said seal are withdrawn into said coupling means as the seal displacement means moves from the ready state to the deployed state.

23. A valve as claimed in claim 19 in which said actuator includes a safety lock means for preventing undesired movement of the seal displacement means.

24. A valve as claimed in claim 19 in which said safety lock means comprises a tongue releaseably engageable with said seal displacement means for preventing movement from the ready state to the deployed state.

25. A valve as claimed in claim 19 including stop means for preventing said actuator from moving in a reverse direction which would return the valve from the deployed state to the ready state.

26. A valve as claimed in claim 19 including visible or tactile indication means for indicating to a user the position of the valve between its ready and deployed states.

27. A valve as claimed in claim 19, wherein said seal displacement means includes a first and a second internal seal arranged concentrically between said body and said seal displacement means, and longitudinally between said first and second open ends, wherein said first and second seal are separated by a distance parallel to the longitudinal axis of said displacement means.

28. A valve as claimed in claim 27, in which said distance separating said first and second seal is greater than the distance the seal displacement means moves from the ready state to the deployed state.

29. A valve as claimed in claim 19 in which the valve further includes a seal displacement means movable a predetermined distance within the body so as to interrupt the seal permitting fluid to pass along the passageway between the ends, wherein said seal displacement means further includes a first and a second internal seal arranged concentrically between said body and said seal displacement means, and longitudinally between said first and second open ends, wherein said first and second seal are separated by a distance parallel to the longitudinal axis of said displacement means.

30. A valve as claimed in claim 29, in which said distance separating said first and second seal is greater than said predetermined distance.

31. A valve comprising a body having first and second open ends and a passageway for fluid between the ends, said first end including a coupling means for sealingly connecting said body about an opening of an external device and a seal blocking said open area of said first end which in use is placeable in register with said opening of said external device, said valve further including a seal displacement means movable within said body so as to interrupt said seal permitting fluid to pass along the passageway between said ends, said coupling means and seal presenting an external sterilisable mating surface for sealingly mating with a mating surface about said opening in said external device;

in which said displacement means comprises a means for rupturing said seal so as to allow fluid communication between said interiors of said body and said external device; and in which said rupturing means comprises a hollow piston which has an open end comprising said second open end of said valve body.

* * * * *